US012351854B2

(12) United States Patent
Mouri et al.

(10) Patent No.: US 12,351,854 B2
(45) Date of Patent: Jul. 8, 2025

(54) TRANSFORMED MICROORGANISM AND METHOD OF PRODUCING POLYHYDROXYALKANOATE USING THE MICROORGANISM

(71) Applicant: KANEKA CORPORATION, Osaka (JP)

(72) Inventors: Yoshihiro Mouri, Takasago (JP); Hisashi Arikawa, Takasago (JP); Shunsuke Sato, Takasago (JP)

(73) Assignee: KANEKA CORPORATION, Osaka (JP)

( * ) Notice: Subject to any disclaimer, the term of this patent is extended or adjusted under 35 U.S.C. 154(b) by 617 days.

(21) Appl. No.: 17/641,358

(22) PCT Filed: Aug. 4, 2020

(86) PCT No.: PCT/JP2020/029763
§ 371 (c)(1),
(2) Date: Mar. 8, 2022

(87) PCT Pub. No.: WO2021/049207
PCT Pub. Date: Mar. 18, 2021

(65) Prior Publication Data
US 2022/0315958 A1 Oct. 6, 2022

(30) Foreign Application Priority Data
Sep. 9, 2019 (JP) .................. 2019-163743

(51) Int. Cl.
*C12P 7/625* (2022.01)
*C12N 1/20* (2006.01)
*C12N 1/21* (2006.01)
*C12N 9/10* (2006.01)
*C12N 15/74* (2006.01)

(52) U.S. Cl.
CPC ............. *C12P 7/625* (2013.01); *C12N 1/20* (2013.01); *C12N 9/1029* (2013.01); *C12N 15/74* (2013.01); *C12N 2800/101* (2013.01)

(58) Field of Classification Search
None
See application file for complete search history.

(56) References Cited

U.S. PATENT DOCUMENTS

| 2018/0163236 A1* | 6/2018 | Taguchi | .................. C12N 15/70 |
| 2020/0340020 A1 | 10/2020 | Arikawa et al. | |

FOREIGN PATENT DOCUMENTS

| CN | 105779488 A | 7/2016 |
| WO | WO 2016/194771 A1 | 12/2016 |
| WO | WO 2019/142845 A1 | 7/2019 |

OTHER PUBLICATIONS

Uniprot, Accession No. Q0KBU9, 2018, www.uniprot.org. (Year: 2018).*
Uniprot, Accession No. Q0K924, 2018, www.uniprot.org. (Year: 2018).*
Uniprot, Accession No. B3R4M9, 2018, www.uniprot.gov. (Year: 2018).*
Uniprot, Accession No. A0A370NYX5, 2018, www.uniprot.gov. (Year: 2018).*
Wheeler, Selecting the right protein-scoring matrix, Unit 3.5.1-3.5.6, Current Protocols in Bioinformatics, 2003. (Year: 2003).*
Reeck et al., Homology in proteins and nucleic acids, Cell 50, 1987, 667. (Year: 1987).*
Kalia et al., Manipulating Microbial Cell Morphology for the Sustainable Production of Biopolymers, Polymers 16, 2024, 410 (Year: 2024).*
International Search Report mailed on Sep. 8, 2020 in PCT/JP2020/029763 filed on Aug. 4, 2020 (3 pages).
Zhang, X.-C. et al., "Engineering cell wall synthesis mechanism for enhanced PHB accumulation in *E. coli*", Metabolic Engineering, Nov. 24, 2017, vol. 45, pp. 32-42.
UniProtKB, Accesion No. Q0KBU9, H16_A1386 gene, [online], Last sequence update: Oct. 3, 2006, [retrieved on Aug. 25, 2020], URL:https://www.uniprot.org/uniprot/Q0KBU9, total 5 pages.
UniProtKB, Accesion No. Q0K924, H16_A2405 gene, [online], Last sequence update: Oct. 3, 2006, [retrieved on Aug. 25, 2020], URL:https://www.uniprot.org/uniprot/Q0K924; total 4 pages.
Shen, R. et al., "Manipulation of polyhydroxyalkanoate granular sizes in *Halomonas bluephagenesis*", Metabolic Engineering, Apr. 6, 2019, vol. 54, pp. 117-126.
Anderson, A.J. et al., "Biosynthesis and composition of bacterial poly(hydroxyalkanoates)", Int. J. Biol. Macromol., Apr. 1990, vol. 12, pp. 102-105.
Sato, S. et al., "Regulation of 3-hydroxyhexanoate composition in PHBH synthesized by recombinant *Cupriavidus necator* H16 from plant oil by using butyrate as a co-substrate", Journal of Bioscience and Bioengineering, 2015, vol. 120, No. 3, pp. 246-251.
Insomphun, C. et al., "Improved artificial pathway for biosynthesis of poly (3-hydroxybutyrate-co-3-hydroxyhexanoate) with high $C_6$-monomer composition from fructose in *Ralstonia eutropha*", Metabolic Engineering, 2015, vol. 27, pp. 38-45.

* cited by examiner

Primary Examiner — Todd M Epstein
(74) Attorney, Agent, or Firm — Oblon, McClelland, Maier & Neustadt, L.L.P.

(57) ABSTRACT

Provided is a transformed microorganism that has a polyhydroxyalkanoate synthase gene and in which expression of an A1386 gene and/or an A2405 gene is reduced. In the transformed microorganism, expression of a minC gene and a minD gene may be enhanced. Also provided is a method of producing a PHA, the method including the step of culturing the transformed microorganism in the presence of a carbon source.

15 Claims, 6 Drawing Sheets

Specification includes a Sequence Listing.

Comparative Example 1

Comparative Example 2

Comparative Example 3

Comparative Example 4

Example 1

Example 2

Example 3

Example 4

Example 5

Example 6

Example 7

TRANSFORMED MICROORGANISM AND METHOD OF PRODUCING POLYHYDROXYALKANOATE USING THE MICROORGANISM

REFERENCE TO A SEQUENCE LISTING

The Sequence Listing for this application is submitted as an ASCII text file named 541839US_SL.TXT, created on Mar. 8, 2022, and having a size of 45,998 bytes. The content of the ASCII text file is incorporated herein by reference in its entirety.

TECHNICAL FIELD

The present invention relates to a transformed microorganism and a method of producing a polyhydroxyalkanoate using the microorganism.

BACKGROUND ART

There is a growing awareness of environmental issues, food issues, health, and safety, and more and more people are becoming nature-oriented. Against such a background, material production using microorganisms (such as fermentative production and bioconversion) is becoming increasingly significant and important. Microbial material production is applied also to production of protein pharmaceuticals and production of nucleic acids for gene therapy. For example, ethanol production, acetic acid production, and medical protein production using microorganisms such as yeasts and bacteria are actively employed on an industrial scale.

An example of the microbial material production is microbial production of polyhydroxyalkanoates (also referred to as "PHAs" hereinafter) which are considered promising biodegradable plastics for industrial use (see Non Patent Literature 1). PHAs are thermoplastic polyesters produced and accumulated as energy storage materials in cells of many kinds of microorganisms and are biodegradable. Nowadays, the heightened environmental awareness has led to increasing attention to non-petroleum-based plastics. In particular, there is a strong demand for practical use of PHAs produced and accumulated in microorganisms because such PHAs are absorbed into the carbon circulation process in the nature and are therefore expected to have little adverse impact on the ecosystems. A known example of PHA production using microorganisms is to produce a PHA by feeding bacteria of the genus *Cupriavidus* with a carbon source such as a sugar, vegetable oil, or fatty acid and thus allowing the bacteria to accumulate the PHA in their cells (see Non Patent Literatures 2 and 3).

However, microbial material production requires the complicated steps of separating and collecting the microbial cells and the target product and could suffer the problem of high production cost. Improving the efficiency of separation and collection is a major challenge to be addressed for production cost reduction.

In the context of cell size increase of microorganisms that produced PHAs, it is known that the cell size of a microorganism that produced a PHA is increased, for example, by overexpressing minCD which is a protein acting as a cell division inhibitor or by disrupting monofunctional peptidoglycan glycosyltransferase which is a peptidoglycan synthase (see Non Patent Literature 4 and Patent Literature 1). However, there has been no report of the association between a peptidoglycan hydrolase and the cell morphology of a microorganism that produced a PHA.

CITATION LIST

Non Patent Literature

NPL 1: Anderson AJ., et al., *Int. J. Biol. Macromol.*, 12, 102-105 (1990)
NPL 2: Sato S., et al., *J. Biosci. Bioeng.*, 120 (3), 246-251 (2015)
NPL 3: Insomphun C., et al., *Metab. Eng.*, 27, 38-45 (2015)
NPL 4: Shen R., et al., *Metab. Eng.*, 54, 117-126 (2019)
PTL 1: WO 2016/194771

SUMMARY OF INVENTION

Technical Problem

A PHA is accumulated in microbial cells. To use the PHA accumulated in the microbial cells as a biodegradable plastic, it is necessary first to separate and collect the microbial cells from the culture fluid. The separation and collection of the microbial cells can be conducted by means such as a centrifuge or separation membrane, and the ease and efficiency of the separation and collection depend on the size of the microbial cells. That is, a larger size of the microbial cells allows the separation and collection to be more easily and efficiently accomplished by means such as a centrifuge or separation membrane, leading to a lower production cost.

In view of the above circumstances, the present invention aims to provide a transformed microorganism that accumulates a PHA and whose cell size can be large and a method of producing the PHA using the transformed microorganism.

Solution to Problem

The present inventors conducted a study using a bacterium of the genus *Cupriavidus*, in which expression of any of A0302, A0597, A1386, A2272, and A2405 genes, which are considered to encode peptidoglycan hydrolases, was reduced. As a result, the present inventors have found that when the expression of the A1386 gene or the A2405 gene is reduced in the bacterium, the size of the microbial cells can be increased while ensuring an industrially desired level of PHA accumulation. Based on this finding, the inventors have arrived at the present invention. The present inventors have also found that the size of the microbial cells can be further increased by enhancing the expression of minC and minD genes in addition to reducing the expression of the A1386 gene or the A2405 gene. Based on this finding, the inventors have arrived at the present invention.

Specifically, the present invention relates to a transformed microorganism having a polyhydroxyalkanoate synthase gene, wherein expression of an A1386 gene and/or an A2405 gene is reduced. Preferably, the A1386 gene is a gene that encodes an amino acid sequence that is at least 85% homologous to the amino acid sequence of SEQ ID NO: 1, and the A2405 gene is a gene that encodes an amino acid sequence that is at least 85% homologous to the amino acid sequence of SEQ ID NO: 2. In the transformed microorganism, expression of a minC gene and a minD gene may be enhanced. Preferably, the minC gene is a gene that encodes an amino acid sequence that is at least 85% homologous to the amino acid sequence of SEQ ID NO: 3, and the minD gene is a gene that encodes an amino acid sequence that is at least 85% homologous to the amino acid sequence of SEQ ID NO: 4. The transformed microorganism preferably belongs to the genus *Cupriavidus*, and is more preferably transformed *Cupriavidus necator*. The present invention further relates to a method of producing a polyhydroxyalkanoate, the method including the step of culturing the transformed microorganism in the presence of a carbon source. The polyhydroxyalkanoate is preferably a copolymer of two or more hydroxyalkanoates, more preferably a copolymer containing 3-hydroxyhexanoate as a monomer unit, and even more preferably a copolymer of 3-hydroxybutyrate and 3-hydroxyhexanoate.

Advantageous Effects of Invention

The present invention can provide a transformed microorganism that accumulates a PHA and whose cell size can be large and a method of producing the PHA using the transformed microorganism. In the present invention, since the size of microbial cells accumulating the PHA is large, the microbial cells can easily be separated and collected from a culture fluid, and the production cost can be reduced.

DESCRIPTION OF EMBODIMENTS

Figure 1:
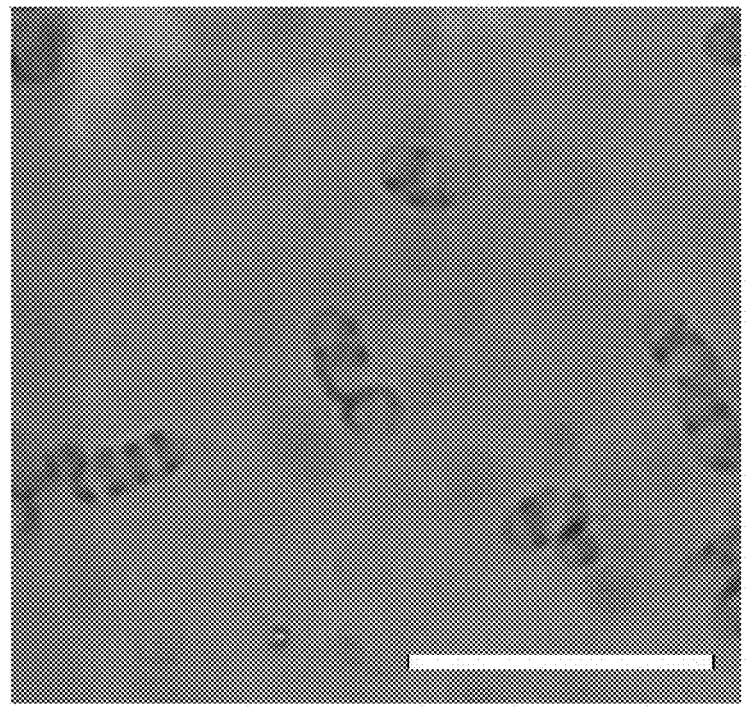
FIG. 1 is a microscope image of a KNK-005 strain which was cultured (Comparative Example 1), where the scale bar represents 10 µm (the same applies to FIGS. 2 to 11).

Hereinafter, an embodiment of the present invention will be described in detail.

A transformed microorganism according to the present embodiment is a transformed microorganism that has a PHA synthase gene and in which expression of an A1386 gene and/or an A2405 gene is reduced. In the transformed microorganism, expression of minC and minD genes may be enhanced.

(Microorganism)

The transformed microorganism according to the present embodiment may be a microorganism having a PHA synthase gene and transformed to reduce the expression of the A1386 gene. Alternatively, the transformed microorganism may be a microorganism having a PHA synthase gene and transformed to reduce the expression of the A2405 gene. Alternatively, the transformed microorganism may be a microorganism having a PHA synthase gene and transformed to reduce the expression of the A1386 gene and enhance the expression of the minC and minD genes. Alternatively, the transformed microorganism may be a microorganism having a PHA synthase gene and transformed to reduce the expression of the A2405 gene and enhance the expression of the minC and minD genes. Alternatively, the transformed microorganism may be a microorganism having a PHA synthase gene and transformed to reduce the expression of the A1386 and A2405 genes. Alternatively, the transformed microorganism may be a microorganism having a PHA synthase gene and transformed to reduce the expression of the A1386 and A2405 genes and enhance the expression of the minC and minD genes.

The host of the transformed microorganism according to the present embodiment is not limited to a particular type, but preferably a bacterium having the A1386 gene, A2405 gene, minC gene, or minD gene. Preferred examples of the bacterium include bacteria belonging to the family Burkholderiaceae such as bacteria of the genus *Ralstonia*, the genus *Cupriavidus*, the genus *Wautersia*, and the genus *Burkholderia*. In view of safety and PHA productivity, bacteria belonging to the genus *Ralstonia* and the genus *Cupriavidus* are more preferred. Even more preferred are bacteria belonging to the genus *Cupriavidus*. Particularly preferred is *Cupriavidus necator*.

The host of the transformed microorganism according to the present embodiment may be a wild strain inherently having a PHA synthase gene, a mutant strain obtained by artificially mutating the wild strain, or a strain having a foreign PHA synthase gene introduced by a genetic engineering technique. The method of introducing the foreign PHA synthase gene is not limited to a particular technique, and the introduction method can be selected from: a method in which the foreign gene is directly inserted onto a chromosome of the host or a gene on the chromosome is replaced by the foreign gene; a method in which the foreign gene is directly inserted onto a megaplasmid possessed by the host or a gene on the megaplasmid is replaced by the foreign gene; and a method in which the foreign gene is placed on a vector such as a plasmid, phage, or phagemid and the vector with the gene is introduced into the host. Two or more of these methods may be used in combination. In view of the stability of the introduced gene, it is preferable to use the method in which the foreign gene is directly inserted onto a chromosome of the host or a gene on the chromosome is replaced by the foreign gene or the method in which the foreign gene is directly inserted onto a megaplasmid possessed by the host or a gene on the megaplasmid is replaced by the foreign gene, and it is more preferable to use the method in which the foreign gene is directly inserted onto a chromosome of the host or a gene on the chromosome is replaced by the foreign gene.

(PHA Synthase Gene)

The PHA synthase gene is not limited to a particular type, and examples of the PHA synthase gene include PHA synthase genes derived from living organisms belonging to the genus *Ralstonia*, the genus *Cupriavidus*, the genus *Wautersia*, the genus *Alcaligenes*, the genus *Aeromonas*, the genus *Pseudomonas*, the genus *Nocardia*, and the genus *Chromobacterium*, and further include altered genes resulting from alteration of the mentioned PHA synthase genes. Such an altered gene may be a gene having a base sequence that encodes a PHA synthase in which one or more amino acid residues are deleted, added, inserted, or replaced. Examples of the PHA synthase gene include a gene having a base sequence that encodes a polypeptide represented by the amino acid sequence of any one of SEQ ID NOS: 5 to 9 and a gene having a base sequence that encodes a polypeptide having PHA synthase activity and represented by an amino acid sequence that is at least 85% homologous to the amino acid sequence of any one of SEQ ID NOS: 5 to 9. The sequence homology is preferably 90% or more, more preferably 95% or more, even more preferably 97% or more, and particularly preferably 99% or more.

(PHA)

The PHA produced by the transformed microorganism according to the present embodiment is not limited to a particular type, and may be any PHA that can be produced by microorganisms. The PHA is preferably any one of the following polymers: a homopolymer of one monomer selected from 3-hydroxyalkanoates having 4 to 16 carbon atoms; a copolymer of one monomer selected from 3-hydroxyalkanoates having 4 to 16 carbon atoms and another hydroxyalkanoate (such as a 2-hydroxyalkanoate, 4-hydroxyalkanoate, 5-hydroxyalkanoate, or 6-hydroxyalkanoate having 4 to 16 carbon atoms); and a copolymer of two or more monomers selected from 3-hydroxyalkanoates having 4 to 16 carbon atoms. Examples of the PHA include, but are not limited to: P(3HB) which is a homopolymer of 3-hydroxybutyrate (abbreviated as 3HB); P(3HB-co-3HV) which is a copolymer of 3HB and 3-hydroxyvalerate (abbreviated as 3HV); P(3HB-co-3HH) (abbreviated as PHBH) which is a copolymer of 3HB and 3-hydroxyhexanoate (abbreviated as 3HH); P(3HB-co-4HB) which is a copolymer of 3HB and 4-hydroxybutyrate (abbreviated as 4HB); and a PHA containing lactic acid (abbreviated as LA) as a constituent component (an example of this PHA is P(LA-co-3HB) which is a copolymer of 3HB and LA). Among these examples, PHBH is preferred in that this polymer has a wide range of applications. The type of the PHA to be produced can be appropriately selected according to the intended purpose and depending on the type of the PHA synthase gene possessed by or introduced into the microorganism used, the type of the metabolizing gene involved in synthesis of the PHA, and the culture conditions.

(Peptidoglycan)

Peptidoglycan is a main component of bacterial cell walls and a kind of polymer compound composed of peptides and sugars. The structure of peptidoglycan varies for different bacteria. In Escherichia coli, which is a typical example of bacteria, peptidoglycan is composed of: sugar chains of two alternating amino sugars, namely N-acetylglucosamine (GlcNAc) and N-acetylmuramic acid (MurNAc); and pentapeptides represented by L-alanine (L-Ala)-γ-D-glutamic acid (Glu)-meso-diaminopimelic acid (m-DAP)-D-alanine (D-Ala)-D-Ala. L-Ala of each pentapeptide is attached to MurNAc of one of the sugar chains by peptide binding. D-Ala is removed from the pentapeptide, m-DAP of the resulting tetrapeptide and D-Ala of a tetrapeptide of another sugar chain are bonded, and the two sugar chains are cross-linked to form a strong structure.

(Peptidoglycan Hydrolase)

Many bacteria have a plurality of peptidoglycan hydrolases such as N-acetylmuramoyl-L-alanine amidase, D-alanyl-D-alanine endopeptidase, and D-alanyl-D-alanine carboxypeptidase. N-acetylmuramoyl-L-alanine amidase breaks N-terminal bonds between MurNAc and L-Ala in peptidoglycan. D-alanyl-D-alanine-endopeptidase breaks, for example, m-DAP-to-D-Ala bonds present in crosslinked portions between tetrapeptides. D-alanyl-D-alanine-carboxypeptidase breaks D-Ala-to-D-Ala bonds in pentapeptides and removes the terminal D-Ala.

According to the UniProtKB database, the protein encoded by the A0597 gene (UniProtKB ID: Q0KEW8) of Cupriavidus necator is considered N-acetylmuramoyl-L-alanine amidase.

According to the UniProtKB database, the protein encoded by the A0302 gene (UniProtKB ID: Q0KE26) and A1386 gene (UniProtKB ID: Q0KBU9) of Cupriavidus necator is considered D-alanyl-D-alanine carboxypeptidase.

According to the UniProtKB database, the A2272 and A2405 genes of Cupriavidus necator are considered to encode a hydrolase related to the cell wall. However, the details of the functions of these genes are not reported.

The A1386 gene has a base sequence that encodes a polypeptide represented by the amino acid sequence of SEQ ID NO: 1 or a polypeptide represented by an amino acid sequence that is at least 85% homologous to the amino acid sequence of SEQ ID NO: 1. The sequence homology is preferably 90% or more, more preferably 95% or more, even more preferably 97% or more, and particularly preferably 99% or more. The sequence homology between the amino acid sequence of SEQ ID NO: 1 and the amino acid sequence of the protein encoded by the A0302 gene is about 30%.

The A2405 gene has a base sequence that encodes a polypeptide represented by the amino acid sequence of SEQ ID NO: 2 or a polypeptide represented by an amino acid sequence that is at least 85% homologous to the amino acid sequence of SEQ ID NO: 2. The sequence homology is preferably 90% or more, more preferably 95% or more, even more preferably 97% or more, and particularly preferably 99% or more. The sequence homology between the amino acid sequence of SEQ ID NO: 2 and the amino acid sequence of the protein encoded by the A2272 gene is about 40%.

(minC and minD Genes)

Proteins MinC, MinD, and MinE encoded by minC, minD, and minE genes are proteins that cooperate in bacteria to control cell division (MinCDE system). For example, it is known that in cells of Escherichia coli, the MinD forms a polymer in an ATP-dependent manner, further forms a complex with the MinC, and rapidly oscillates between the cell poles. The MinC serves to inhibit septum formation during cell division. The MinE is known to bind to the MinD competitively against the MinC, and serves to regulate septum formation so that the septum is formed only at the center of the cell.

The minC gene in the present disclosure is a gene having a base sequence that encodes a polypeptide (UniProtKB ID: Q0KFI3) represented by the amino acid sequence of SEQ ID NO: 3 or a polypeptide represented by an amino acid sequence that is at least 85% homologous to the amino acid sequence of SEQ ID NO: 3. The sequence homology is preferably 90% or more, more preferably 95% or more, even more preferably 97% or more, and particularly preferably 99% or more.

The minD gene in the present disclosure is a gene having a base sequence that encodes a polypeptide (UniProtKB ID: Q0KFI4) represented by the amino acid sequence of SEQ ID NO: 4 or a polypeptide represented by an amino acid sequence that is at least 85% homologous to the amino acid sequence of SEQ ID NO: 4. The sequence homology is preferably 90% or more, more preferably 95% or more, even more preferably 97% or more, and particularly preferably 99% or more.

(Gene Expression Reduction)

"Reduced gene expression" in the present disclosure means a state in which the level of transcription of a target gene or the level of expression of a polypeptide encoded by the target gene is decreased as compared to that in a strain in which the expression of the target gene is not reduced. The amount of decrease is not limited to a particular range, and it is sufficient that the level of transcription of the target gene or the level of expression of the polypeptide be less than that in the strain in which the expression of the target gene is not reduced. The level of transcription of the target gene or the level of expression of the polypeptide is preferably 0.8 or less times, more preferably 0.5 or less times, even more preferably 0.3 or less times, and still even more preferably 0.2 or less times that in the strain in which the expression of the target gene is not reduced. The level of transcription of the target gene or the level of expression of the polypeptide encoded by the target gene may be zero. The gene expression can be considered to have been reduced also when the polypeptide encoded by the target gene cannot exhibit the original function for a reason such as alteration of the base sequence of the gene. In the case of the microorganism having a PHA synthase gene, the expression of the target gene can be reduced by genetically altering the microorganism so that the microorganism will produce a metabolite or protein that inhibits the function of the corresponding polypeptide.

In the present embodiment, the method of gene expression reduction is not limited to a particular technique, and examples of the method include: a method in which a part or the entire length of the target gene is deleted; a method in which the "gene expression regulatory sequence" responsible for the expression of the target gene is altered; and a method in which the target gene and/or a base sequence neighboring the target gene is altered to decrease the stability of the transcribed messenger RNA. The method of base sequence alteration is not limited to a particular technique, and the base sequence alteration can be accomplished through replacement, deletion, insertion, and/or addition made to at least a part of the target gene and/or the neighboring base sequence. The replacement, deletion, insertion, and/or addition can be made by any method known to those skilled in the art. In the case of the transformed microorganism having a PHA synthase gene, an antisense RNA, RNA interference (RNAi), or CRISPR interference (CRISPRi) may be used to reduce the expression of the target gene without altering the target gene and/or the neighboring base sequence.

(Gene Expression Enhancement)

Enhanced gene expression in the present disclosure means a state in which the level of transcription of a target gene or the level of expression of a polypeptide encoded by the target gene is increased as compared to that in a strain in which the expression of the target gene is not enhanced. The amount of increase is not limited to a particular range, and it is sufficient that the level of transcription of the target gene or the level of expression of the polypeptide be more than that in the strain in which the expression of the target gene is not enhanced. The level of transcription of the target gene or the level of expression of the polypeptide is preferably 1.1 or more times, more preferably 1.2 or more times, even more preferably 1.5 or more times, and still even more preferably 2 or more times that in the strain in which the expression of the target gene is not enhanced.

In the present embodiment, the method of enhancing the expression of the minC and minD genes is not limited to a particular technique, and the enhancement method can be selected from a method in which the target gene is introduced into the host and a method in which the level of expression of the target gene inherently possessed by the host on the genome DNA is increased. Both of the two methods may be used in combination.

The method of introducing the target gene into the host is not limited to a particular technique, and the introduction method can be selected from: a method in which the target gene is directly inserted onto a chromosome of the host or a gene on the chromosome is replaced by the target gene; a method in which the target gene is directly inserted onto a megaplasmid possessed by the host or a gene on the megaplasmid is replaced by the target gene; and a method in which the target gene is placed on a vector such as a plasmid, phage, or phagemid and the vector with the gene is introduced into the host. Two or more of these methods may be used in combination.

In view of the stability of the introduced gene, it is preferable to use the method in which the target gene is directly inserted onto a chromosome of the host or a gene on the chromosome is replaced by the target gene or the method in which the target gene is directly inserted onto a megaplasmid possessed by the host or a gene on the megaplasmid is replaced by the target gene, and it is more preferable to use the method in which the target gene is directly inserted onto a chromosome of the host or a gene on the chromosome is replaced by the target gene. For reliable expression of the introduced gene, it is preferable to introduce the target gene in such a manner that the target gene is located downstream of a "gene expression regulatory sequence" inherently possessed by the host or downstream of a foreign "gene expression regulatory sequence". A "gene expression regulatory sequence" in the present disclosure is a DNA sequence containing a base sequence that controls the level of transcription of the gene (an example of this base sequence is a promotor sequence) and/or a base sequence that regulates the level of translation of a messenger RNA transcribed from the gene (an example of this base sequence is a Shine-Dalgarno sequence). The "gene expression regulatory sequence" used may be any suitable naturally-occurring base sequence or an artificially constructed or altered base sequence.

The method of increasing the level of expression of the target gene inherently possessed by the host on the genome DNA is not limited to a particular technique, and examples include: a method in which a "gene expression regulatory sequence" upstream of the target gene is altered; a method in which a foreign "gene expression regulatory sequence" is introduced upstream of the target gene; and a method in which the target gene and/or a base sequence neighboring the target gene is altered to increase the stability of the transcribed messenger RNA.

Examples of the promotor sequence or Shine-Dalgarno sequence contained in the "gene expression regulatory sequence" include, but are not limited to, the base sequences of SEQ ID NOS: 10 to 16 and base sequences containing any part of the base sequences of SEQ ID NOS: 10 to 16.

Replacement, deletion, insertion, and/or addition made to at least a part of the genome DNA can be accomplished using methods known to those skilled in the art. Typical methods include a method using a transposon and the mechanism of homologous recombination (Ohman et al., *J. Bacteriol.*, 162:1068-1074 (1985)) and a method based on site-specific integration caused by the mechanism of homologous recombination and on loss due to second homologous recombination (Noti et al., *Methods Enzymol.*, 154:197-217 (1987)). A method may also be used in which a sacB gene derived from *Bacillus subtilis* is allowed to coexist and thus in which a microorganism strain having lost a gene due to second homologous recombination is easily isolated as a sucrose-resistant strain (Schweizer, *Mol. Microbiol.*, 6:1195-1204 (1992) or Lenz et al., *J. Bacteriol.*, 176:4385-4393 (1994)). Another alternative method is to use a CRISPR/Cas9 system-based genome-editing technology for altering the target DNA (Y. Wang et al., *ACS Synth Biol.*, 2016, 5 (7): 721-732). In the CRISPR/Cas9 system, the guide RNA (gRNA) has a sequence capable of binding to a part of the base sequence of the genome DNA to be altered, and serves to transport the Cas9 to the target.

The method of introducing a vector into a cell is not limited to a particular technique, and examples of the method include calcium chloride transformation, electroporation, polyethylene glycol transformation, and spheroplast transformation.

Culturing the transformed microorganism according to the present embodiment allows the microbial bodies to accumulate a PHA therein. The culture of the transformed microorganism according to the present embodiment can be conducted by a common microbial culture method, and it is sufficient that the transformed microorganism be cultured in a culture medium containing a suitable carbon source. There are no particular limitations on the composition of the culture medium, the method of adding the carbon source, the scale of the culture, the conditions of aeration and stirring, the culture temperature, and the culture time. It is preferable to add the carbon source to the culture medium continuously or intermittently.

The carbon source used for the culture may be any carbon source that can be assimilated by the transformed microorganism according to the present embodiment. Examples of the carbon source include, but are not limited to: sugars such as glucose, fructose, and sucrose; oils such as palm and palm kernel oils (including palm olein, palm double olein, and palm kernel olein which are low-melting fractions obtained through fractionation of palm oil and palm kernel oil), corn oil, coconut oil, olive oil, soybean oil, rapeseed oil, and Jatropha oil; fractions of these oils; by-products formed during refining of these oils; fatty acids such as lauric acid, oleic acid, stearic acid, palmitic acid, and myristic acid; derivatives of these fatty acids; and glycerol. In the case where the transformed microorganism according to the present embodiment can assimilate gases such as carbon dioxide, carbon monoxide, and methane or alcohols such as methanol and ethanol, any of these gases or alcohols can be used as the carbon source.

In the PHA production according to the present embodiment, it is preferable to culture the microorganism using a culture medium containing the carbon source as described above and other nutrient sources including a nitrogen source, an inorganic salt, and another organic nutrient source. Examples of the nitrogen source include, but are not limited to: ammonia; ammonium salts such as ammonium chloride, ammonium sulfate, and ammonium phosphate; peptone; meat extracts; and yeast extracts. Examples of the inorganic salt include potassium dihydrogen phosphate, sodium dihydrogen phosphate, magnesium phosphate, magnesium sulfate, and sodium chloride. Examples of the other organic nutrient source include: amino acids such as glycine, alanine, serine, threonine, and proline; and vitamins such as vitamin B1, vitamin B12, and vitamin C.

After the microorganism is cultured for an adequate time to allow the microbial bodies to accumulate a PHA therein, the PHA is collected from the microbial bodies using a known method. The method of PHA collection is not limited to a particular technique. For example, the PHA can be collected by a method consisting of: after the culture, separating the microbial bodies from the culture fluid by means such as a centrifuge or separation membrane; drying the separated microbial bodies; extracting the PHA from the dried microbial bodies using an organic solvent such as chloroform; removing cellular components from the PHA-containing organic solvent solution by a process such as filtration; adding a poor solvent such as methanol or hexane to the filtrate to precipitate the PHA; removing the supernatant by a process such as filtration or centrifugation; and drying the precipitated PHA. Alternatively, the PHA may be collected by dissolving cellular components other than the PHA in water with the aid of a surfactant, an alkali, or an enzyme, then separating the PHA particles from the aqueous phase by a process such as filtration or centrifugation, and drying the separated PHA particles.

In the present embodiment, large-size microbial cells accumulating a PHA can be obtained, and the microbial cells can be separated from the culture fluid easily and efficiently thanks to their large size.

EXAMPLES

Hereinafter, the present invention will be described in more detail using examples. The present invention is not limited to the examples. The overall genetic manipulation can be carried out, for example, in a manner as taught in Molecular Cloning (Cold Spring Harbor Laboratory Press (1989)). The enzymes, cloning hosts, and other materials used in the gene manipulation can be purchased from market suppliers and used according to the instructions given by the suppliers. The enzymes are not limited to particular types and may be any enzymes that can be used for gene manipulation.

(Production Example 1) Preparation of A0597-Deletionally Disrupted Strain

First, a plasmid for gene deletion was prepared. The preparation was done as follows. PCR using a synthetic oligo DNA was carried out to obtain a DNA fragment (SEQ ID NO: 17) having base sequences upstream and downstream of the A0597 structural gene. The DNA fragment was digested by a restriction enzyme SwaI, and the resulting DNA fragment was joined by a DNA ligase (Ligation High, manufactured by Toyobo Co., Ltd.) to a vector pNS2X-sacB which is described in Japanese Laid-Open Patent Application Publication No. 2007-259708 and which was also digested by SwaI. Thus, a plasmid vector pNS2X-sacB+A0597UD for gene deletion was prepared which had base sequences upstream and downstream of the A0597 structural gene.

Subsequently, an A0597-deletionally disrupted strain was prepared using the plasmid vector pNS2X-sacB+A0597UD for gene deletional disruption. The preparation was done as follows.

An *Escherichia coli* S17-1 strain (ATCC 47055) was transformed with the plasmid vector pNS2X-sacB+A0597UD for gene deletional disruption, and the resulting transformed microorganism was co-cultured with a KNK-005 strain on Nutrient Agar (manufactured by Difco Laboratories) to effect conjugal transfer. The KNK-005 strain is a transformed strain produced by introducing an *Aeromonas caviae*-derived PHA synthase gene (a gene that encodes a PHA synthase having the amino acid sequence of SEQ ID NO: 7) onto the chromosome of a *Cupriavidus necator* H16 strain, and can be prepared according to the method described in U.S. Pat. No. 7,384,766.

The culture fluid obtained as above was inoculated into a Simmons agar medium (2 g/L sodium citrate, 5 g/L sodium chloride, 0.2 g/L magnesium sulfate heptahydrate, 1 g/L ammonium dihydrogen phosphate, 1 g/L potassium dihydrogen phosphate, 15 g/L agar, pH=6.8) containing 250 mg/L kanamycin, and strains grown on the agar medium were selectively collected. Thus, a strain having the plasmid integrated into the chromosome of the KNK-005 strain was obtained. The obtained strain was cultured on Nutrient Broth (manufactured by Difco Laboratories) for two generations, after which the culture broth was diluted and applied onto Nutrient Agar containing 15% sucrose. Strains grown on Nutrient Agar were obtained as strains having lost the plasmid. PCR and analysis using a DNA sequencer were further carried out to isolate one strain from which the start to stop codons of the A0597 structural gene on the chromosome were deleted. This A0597 gene-deleted strain was named "A0597-deletionally disrupted strain".

(Production Example 2) Preparation of A0302-Deletionally Disrupted Strain

First, a plasmid for gene deletion was prepared. The preparation was done as follows. PCR using a synthetic oligo DNA was carried out to obtain a DNA fragment (SEQ ID NO: 18) having base sequences upstream and downstream of the A0302 structural gene. The DNA fragment was digested by a restriction enzyme SwaI, and the resulting DNA fragment was joined by a DNA ligase (Ligation High, manufactured by Toyobo Co., Ltd.) to a vector pNS2X-sacB which is described in Japanese Laid-Open Patent Application Publication No. 2007-259708 and which was also digested by SwaI. Thus, a plasmid vector pNS2X-sacB+A0302UD for gene deletion was prepared which had base sequences upstream and downstream of the A0302 structural gene.

Next, the plasmid vector pNS2X-sacB+A0302UD for A0302 gene deletion was introduced into a KNK-005 strain by the vector introduction procedures as described in Production Example 1. Further, one strain from which the start to stop codons of the A0302 structural gene on the chromosome were deleted was isolated by the strain isolation procedures as described in Production Example 1. This A0302 gene-deleted strain was named "A0302-deletionally disrupted strain".

(Production Example 3) Preparation of A1386-Deletionally Disrupted Strain

First, a plasmid for gene deletion was prepared. The preparation was done as follows. PCR using a synthetic oligo DNA was carried out to obtain a DNA fragment (SEQ ID NO: 19) having base sequences upstream and downstream of the A1386 structural gene. The DNA fragment was digested by a restriction enzyme SwaI, and the resulting DNA fragment was joined by a DNA ligase (Ligation High, manufactured by Toyobo Co., Ltd.) to a vector pNS2X-sacB which is described in Japanese Laid-Open Patent Application Publication No. 2007-259708 and which was also digested by SwaI. Thus, a plasmid vector pNS2X-sacB+A1386UD for gene deletion was prepared which had base sequences upstream and downstream of the A1386 structural gene.

Next, the plasmid vector pNS2X-sacB+A1386UD for A1386 gene deletion was introduced into a KNK-005 strain by the vector introduction procedures as described in Production Example 1. Further, one strain from which the start to stop codons of the A1386 structural gene on the chromosome were deleted was isolated by the strain isolation procedures as described in Production Example 1. This A1386 gene-deleted strain was named "A1386-deletionally disrupted strain".

(Production Example 4) Preparation of A2272-Insertionally Disrupted Strain

First, a plasmid for A2272 gene insertional disruption was prepared. The preparation was done as follows. PCR using a synthetic oligo DNA was carried out to obtain a DNA fragment (SEQ ID NO: 20) having 47 to 231th bases of the A2272 structural gene. The DNA fragment obtained was digested by a restriction enzyme SwaI. The resulting DNA fragment was joined by a DNA ligase (Ligation High, manufactured by Toyobo Co., Ltd.) to a vector pNS2X-sacB which is described in Japanese Laid-Open Patent Application Publication No. 2007-259708 and which was also digested by SwaI. Thus, a plasmid vector pNS2X-sacB-A2272-indel for gene insertional disruption was prepared which had 47 to 231th bases of the A2272 structural gene.

Next, the plasmid vector pNS2X-sacB-A2272-indel for gene insertional disruption was introduced into a KNK-005 strain by the vector introduction procedures as described in Production Example 1. PCR and analysis using a DNA sequencer were further carried out to isolate one strain in which the A2272 gene was disrupted by insertion of the plasmid into the A2272 structural gene sequence on the chromosome. This A2272 gene-disrupted strain was named "A2272-insertionally disrupted strain".

(Production Example 5) Preparation of A2405-Insertionally Disrupted Strain

First, a plasmid for A2405 gene insertional disruption was prepared. The preparation was done as follows. PCR using a synthetic oligo DNA was carried out to obtain a DNA fragment (SEQ ID NO: 21) having 7 to 204th bases of the A2405 structural gene. The DNA fragment obtained was digested by a restriction enzyme SwaI. The resulting DNA fragment was joined by a DNA ligase (Ligation High, manufactured by Toyobo Co., Ltd.) to a vector pNS2X-sacB which is described in Japanese Laid-Open Patent Application Publication No. 2007-259708 and which was also digested by SwaI. Thus, a plasmid vector pNS2X-sacB-A2405-indel for A2405 gene insertional disruption was prepared which had 7 to 204th bases of the A2405 structural gene.

Next, the plasmid vector pNS2X-sacB-A2405-indel for gene insertional disruption was introduced into a KNK-005 strain by the vector introduction procedures as described in Production Example 1. PCR and analysis using a DNA sequencer were further carried out to isolate one strain in which the A2405 gene was disrupted by insertion of the plasmid into the A2405 structural gene sequence on the chromosome. This A2405 gene-disrupted strain was named "A2405-insertionally disrupted strain".

(Production Example 6) Preparation of A2405-Deletionally Disrupted Strain

First, a plasmid for gene deletion was prepared. The preparation was done as follows. PCR using a synthetic oligo DNA was carried out to obtain a DNA fragment (SEQ ID NO: 22) having base sequences upstream and downstream of the A2405 structural gene. The DNA fragment was digested by a restriction enzyme SwaI, and the resulting DNA fragment was joined by a DNA ligase (Ligation High, manufactured by Toyobo Co., Ltd.) to a vector pNS2X-sacB which is described in Japanese Laid-Open Patent Application Publication No. 2007-259708 and which was also digested by SwaI. Thus, a plasmid vector pNS2X-sacB+A2405UD for gene deletion was prepared which had base sequences upstream and downstream of the A2405 structural gene.

Next, the plasmid vector pNS2X-sacB+A2405UD for A2405 gene deletion was introduced into a KNK-005 strain by the vector introduction procedures as described in Production Example 1. Further, one strain from which the start to stop codons of the A2405 structural gene on the chromosome were deleted was isolated by the strain isolation procedures as described in Production Example 1. This A2405 gene-deleted strain was named "A2405-deletionally disrupted strain".

(Production Example 8) Preparation of A1386-A2405-Double Disrupted Strain

The plasmid vector pNS2X-sacB+A2405-UD for A2405 gene deletion was introduced into the A1386-deletionally disrupted strain by the vector introduction procedures as described in Production Example 1. Further, one strain from which the start to stop codons of the A2405 structural gene on the chromosome were deleted was isolated by the strain isolation procedures as described in Production Example 1. This strain, from which the A1386 and A2405 genes were deleted, was named "A1386-A2405-double disrupted strain".

(Production Example 9) Preparation of minCD-Expressed, A1386-Deletionally Disrupted Strain First, a plasmid vector pNS2X-sacB-PA-minCD for minCD gene expression was prepared. The preparation was done as follows. PCR using a synthetic oligo DNA was carried out to obtain a DNA fragment (SEQ ID NO: 23) having a promoter sequence, a minCD gene sequence, and a base sequence of an integration site on the genome. The DNA fragment was digested by a restriction enzyme SwaI, and the resulting DNA fragment was joined by a DNA ligase (Ligation High, manufactured by Toyobo Co., Ltd.) to a vector pNS2X-sacB which is described in Japanese Laid-Open Patent Application Publication No. 2007-259708 and which was also digested by SwaI. Thus, a plasmid vector pNS2X-PA-minCD for minCD gene expression was prepared.

Next, the plasmid vector pNS2X-sacB-PA-minCD for minCD gene expression was introduced into the A1386-deletionally disrupted strain by the vector introduction procedures as described in Production Example 1. Further, one strain having a chromosome onto which the promoter sequence and the minCD gene sequence were inserted was isolated by the strain isolation procedures as described in Production Example 1. This minCD gene-expressed, A1386-deleted strain was named "minCD-expressed, A1386-disrupted strain".

(Production Example 10) Preparation of minCD-Expressed, A2405-Disrupted Strain

The plasmid vector pNS2X-sacB-PA-minCD for minCD gene expression was introduced into the A2405-deletionally disrupted strain by the vector introduction procedures as described in Production Example 1. Further, one strain having a chromosome onto which the promotor sequence and the minCD gene sequence were inserted was isolated by the strain isolation procedures as described in Production Example 1. This minCD gene-expressed, A2405-deleted strain was named "minCD-expressed, A2405-disrupted strain".

(Production Example 11) Preparation of minCD-Expressed, A2405-A1386-Disrupted Strain The plasmid vector pNS2X-sacB+A1386UD for A1386 gene deletion was introduced into the minCD-expressed, A2405-disrupted strain by the vector introduction procedures as described in Production Example 1. Further, one strain from which the start to stop codons of the A1386 structural gene on the chromosome were deleted was isolated by the strain isolation procedures as described in Production Example 1. This minCD-expressed, A2405-A1386-deleted strain was named "minCD-expressed, A2405-A1386-disrupted strain".

(Comparative Example 1) PHA Production by KNK-005 Strain

Culture examination using a KNK-005 strain was conducted under the conditions described below.
(Culture Media)
The seed culture medium was composed of 1 w/v % Meat-extract, 1 w/v % Bacto-Tryptone, 0.2 w/v % Yeast-extract, 0.9 w/v % $Na_2HPO_4 \cdot 12H_2O$, and 0.15 w/v % $KH_2PO_4$ (pH=6.8).

The preculture medium was composed of 1.1 w/v % $Na_2HPO_4 \cdot 12H_2O$, 0.19 w/v % $KH_2PO_4$, 1.29 w/v % $(NH_4)_2SO_4$, 0.1 w/v % $MgSO_4 \cdot 7H_2O$, 2.5 w/v % palm olein oil, and 0.5 v/v % trace metal salt solution (solution of 1.6 w/v % $FeCl_3 \cdot 6H_2O$, 1 w/v % $CaCl_2 \cdot 2H_2O$, 0.02 w/v % $CoCl_2 \cdot 6H_2O$, 0.016 w/v % $CuSO_4 \cdot 5H_2O$, and 0.012 w/v % $NiCl_2 \cdot 6H_2O$ in 0.1N hydrochloric acid). Palm olein oil was added as a carbon source in a concentration of 10 g/L at one time.

The PHA production culture medium was composed of 0.385 w/v % $Na_2HPO_4 \cdot 12H_2O$, 0.067 w/v % $KH_2PO_4$, 0.291 w/v % $(NH_4)_2SO_4$, 0.1 w/v % $MgSO_4 \cdot 7H_2O$, and 0.5 v/v % trace metal salt solution (solution of 1.6 w/v % $FeCl_3 \cdot 6H_2O$, 1 w/v % $CaCl_2) \cdot 2H_2O$, 0.02 w/v % $CoCl_2 \cdot 6H_2O$, 0.016 w/v % $CuSO_4 \cdot 5H_2O$, and 0.012 w/v % $NiCl_2 \cdot 6H_2O$ in 0.1N hydrochloric acid).
(Method of Measuring Percentage of Accumulated PHA to Dried Microbial Bodies)

The percentage of accumulated PHA to dried microbial bodies was measured as follows. The microbial bodies were collected from the culture fluid by centrifugation. The collected microbial bodies were washed with ethanol and freeze-dried to give dried microbial bodies. To 1 g of the dried microbial bodies was added 100 ml of chloroform, and the microbial bodies in chloroform were stirred at room temperature for a day to extract a PHA from the microbial bodies. The residual microbial bodies were removed by filtration, and the filtrate was concentrated using an evaporator to a total volume of 30 ml. To the concentrate was slowly added 90 ml of hexane, and the mixture was left for 1 hour under gentle stirring. The PHA precipitated was collected by filtration and vacuum-dried at 50° C. for 3 hours. The weight of the dried PHA was measured, and the percentage of the accumulated PHA to the dried microbial bodies was calculated.

(Method of Measuring Cell Size)

The cell size was measured as follows. After the culture, the culture fluid was treated at 65° C. for 60 minutes to inactivate the microbial cells. The treated fluid was analyzed with a laser diffraction-scattering particle size distribution analyzer (Microtrac MT3300EXII manufactured by MicrotracBEL Corporation) to measure the mean volume diameter (MV) of the cells. The measurement was conducted using standard settings (Permeability: Transparent, Particle refractive index: 1.81, Particle shape: Non-spherical, Solvent refractive index: 1.333).

(Microscopic Observation of Cells)

Microscopic observation of the cells was conducted as follows. After the culture, the culture fluid was diluted as appropriate. The dilution was placed and dried on a glass slide, and then the cells were stained with fuchsin. The stained cells were observed with an optical microscope.

(PHA Production Culture)

PHA production culture was performed as follows. First, a glycerol stock (50 μl) of the KNK-005 strain was inoculated into the seed culture medium (10 ml) and cultured for 24 hours to accomplish seed culture. Subsequently, the seed culture fluid was inoculated at a concentration of 1.0 v/v % into a 3 L jar fermenter (MDL-300, manufactured by B.E. Marubishi Co., Ltd.) containing 1.8 L of the preculture medium. The fermenter was operated at a culture temperature of 33° C., a stirring speed of 500 rpm, and an aeration of 1.8 L/min, and the preculture was conducted for 28 hours during which the pH was controlled between 6.7 and 6.8. For the pH control, a 14% aqueous solution of ammonium hydroxide was used.

Next, the preculture fluid was inoculated at a concentration of 5.0 v/v % into a 5 L jar fermenter (MDS-U50, manufactured by B.E. Marubishi Co., Ltd.) containing 2.5 L of the PHA production culture medium. The fermenter was operated at a culture temperature of 33° C., a stirring speed of 420 rpm, and an aeration of 2.1 L/min, and the pH was controlled between 6.7 and 6.8. For the pH control, a 25% aqueous solution of ammonium hydroxide was used. The carbon source was added intermittently. Palm olein oil was used as the carbon source. The culture was continued until the accumulated PHA percentage reached around 90%. The accumulated PHA percentage and the cell size were measured as previously described. The results are listed in Table 1. An image taken by the microscopic cell observation conducted as previously described is shown in FIG. 1.

(Comparative Example 2) PHA Production by A0597-Deletionally Disrupted Strain

Figure 2:
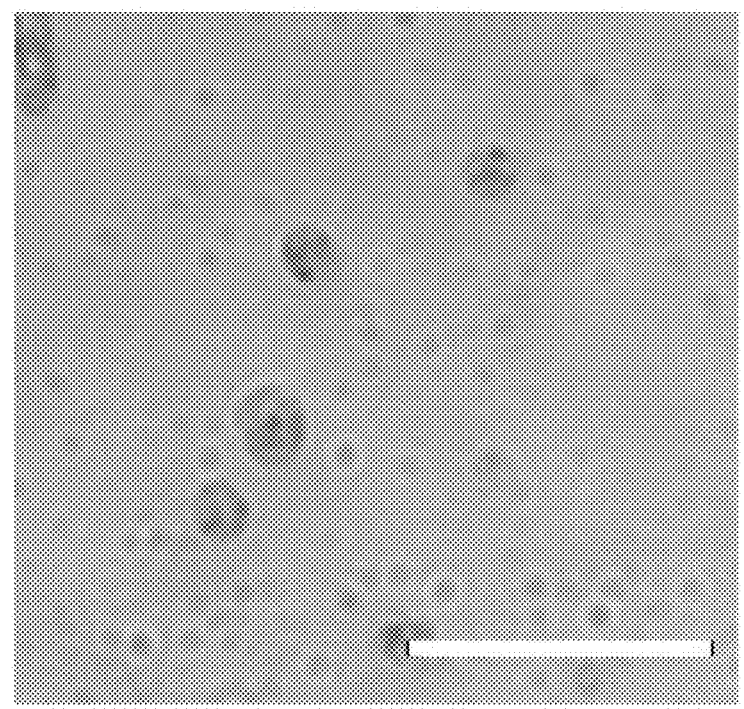
FIG. 2 is a microscope image of an A0597-deletionally disrupted strain which was cultured (Comparative Example 2).

Culture examination using the A0597-deletionally disrupted strain was conducted under the examination conditions as described in Comparative Example 1. The measurement results of the accumulated PHA percentage and the cell size are listed in Table 1. An image taken by the microscopic cell observation conducted as previously described is shown in FIG. 2.

The results of the culture examination revealed that the cell size of the A0597-deletionally disrupted strain, as measured under the conditions previously described, was more than 10% below that of the KNK-005 strain which was a parent strain. The PHA productivity was similar to that of the KNK-005 strain.

(Comparative Example 3) PHA Production by A0302-Deletionally Disrupted Strain

Figure 3:
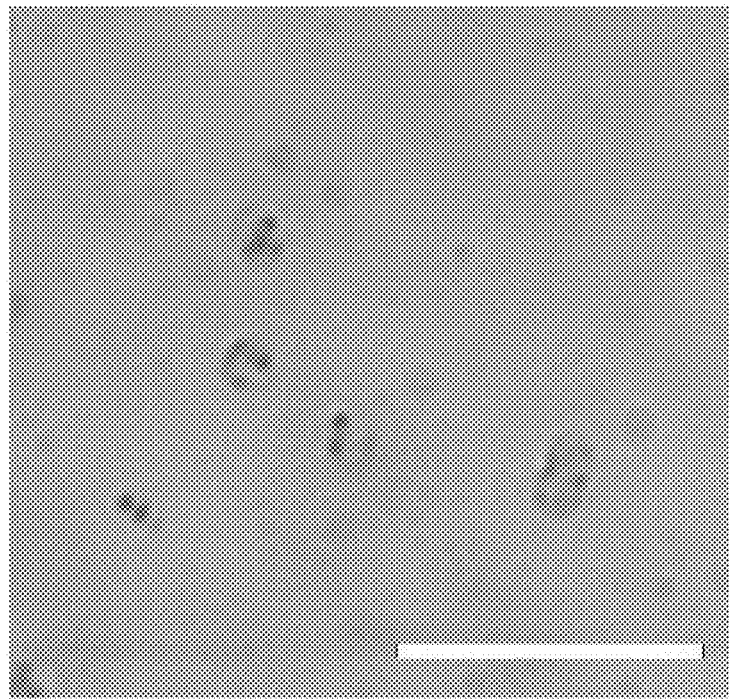
FIG. 3 is a microscope image of an A0302-deletionally disrupted strain which was cultured (Comparative Example 3).

Culture examination using the A0302-deletionally disrupted strain was conducted under the examination conditions as described in Comparative Example 1. The measurement results of the accumulated PHA percentage and the cell size are listed in Table 1. An image taken by the microscopic cell observation conducted as previously described is shown in FIG. 3.

The results of the culture examination revealed that the cell size of the A0302-deletionally disrupted strain, as measured under the conditions previously described, was more than 10% below that of the KNK-005 strain which was a parent strain. The PHA productivity was similar to that of the KNK-005 strain.

(Comparative Example 4) PHA Production by A2272-Insertionally Disrupted Strain

Figure 4:
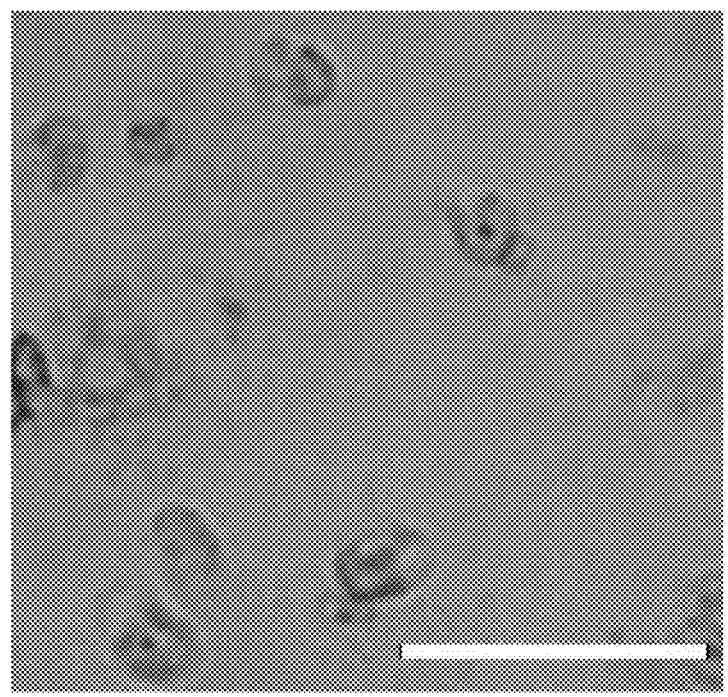
FIG. 4 is a microscope image of an A2272-insertionally disrupted strain which was cultured (Comparative Example 4).

Culture examination using the A2272-insertionally disrupted strain was conducted under the examination conditions as described in Comparative Example 1. The measurement results of the accumulated PHA percentage and the cell size are listed in Table 1. An image taken by the microscopic cell observation conducted as previously described is shown in FIG. 4.

The results of the culture examination revealed that the cell size of the A2272-insertionally disrupted strain, as measured under the conditions previously described, was similar to that of the KNK-005 strain which was a parent strain. The PHA productivity was similar to that of the KNK-005 strain.

(Example 1) PHA Production by A1386-Deletionally Disrupted Strain

Figure 5:
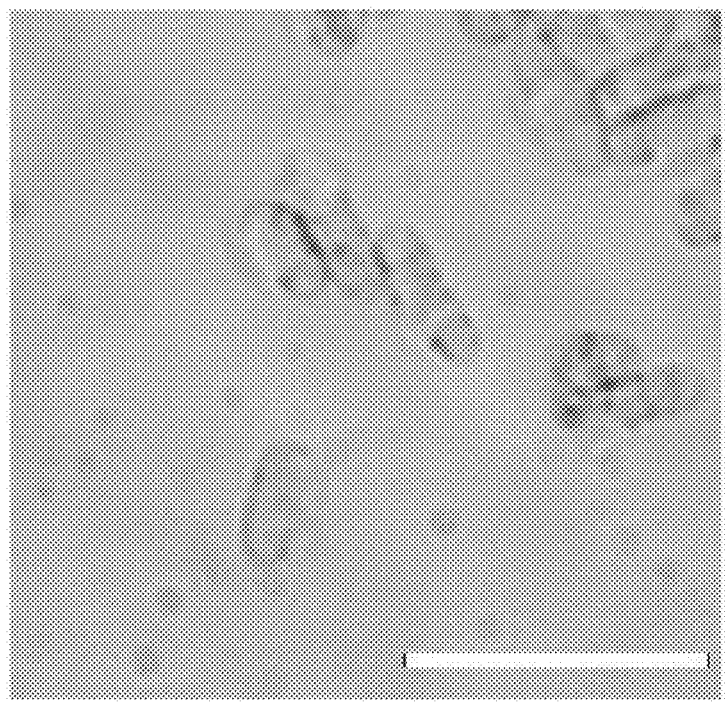
FIG. 5 is a microscope image of an A1386-deletionally disrupted strain which was cultured (Example 1).

Culture examination using the A1386-deletionally disrupted strain was conducted under the examination conditions as described in Comparative Example 1. The measurement results of the accumulated PHA percentage and the cell size are listed in Table 1. An image taken by the microscopic cell observation conducted as previously described is shown in FIG. 5.

The results of the culture examination revealed that the cell size of the A1386-deletionally disrupted strain, as measured under the conditions previously described, was more than 20% above that of the KNK-005 strain which was a parent strain. Additionally, the PHA productivity was comparable to that of the KNK-005 strain.

(Example 2) PHA Production by A2405-Insertionally Disrupted Strain

Figure 6:
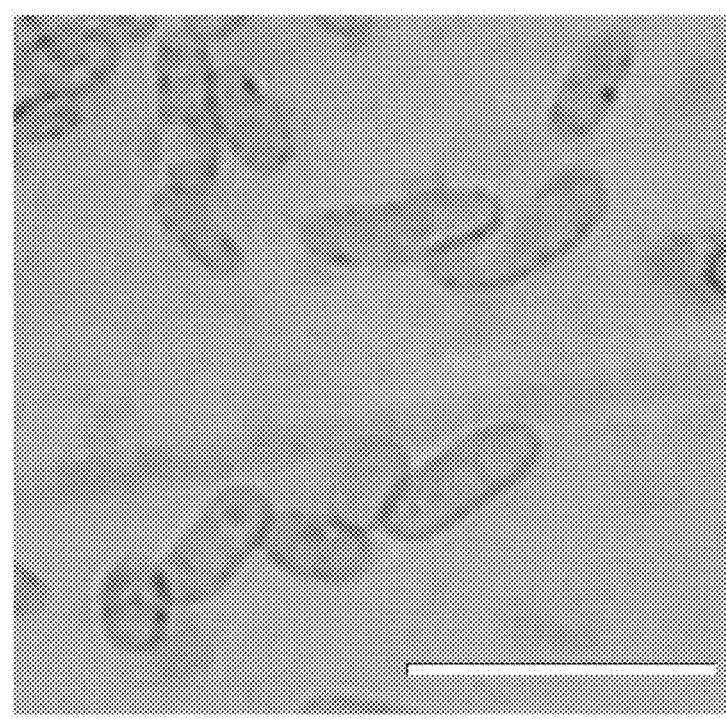
FIG. 6 is a microscope image of an A2405-insertionally disrupted strain which was cultured (Example 2).

Culture examination using the A2405-insertionally disrupted strain was conducted under the examination conditions as described in Comparative Example 1. The measurement results of the accumulated PHA percentage and the cell size are listed in Table 1. An image taken by the microscopic cell observation conducted as previously described is shown in FIG. 6.

The results of the culture examination revealed that the cell size of the A2405-insertionally disrupted strain, as measured under the conditions previously described, was more than 20% above that of the KNK-005 strain which was a parent strain. Additionally, the PHA productivity was comparable to that of the KNK-005 strain.

(Example 3) PHA Production by A2405-Deletionally Disrupted Strain

Figure 7:
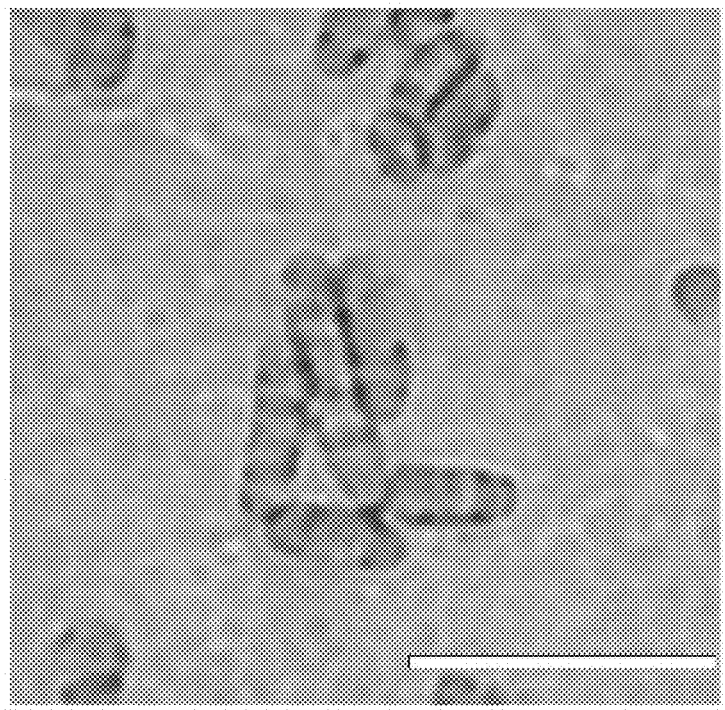
FIG. 7 is a microscope image of an A2405-deletionally disrupted strain which was cultured (Example 3).

Culture examination using the A2405-deletionally disrupted strain was conducted under the examination conditions as described in Comparative Example 1. The measurement results of the accumulated PHA percentage and the cell size are listed in Table 1. An image taken by the microscopic cell observation conducted as previously described is shown in FIG. 7.

The results of the culture examination revealed that the cell size of the A2405-deletionally disrupted strain, as measured under the conditions previously described, was more than 20% above that of the KNK-005 strain which was a parent strain. Additionally, the PHA productivity was comparable to that of the KNK-005 strain.

(Example 4) PHA Production by A1386-A2405-Double Disrupted Strain

Figure 8:
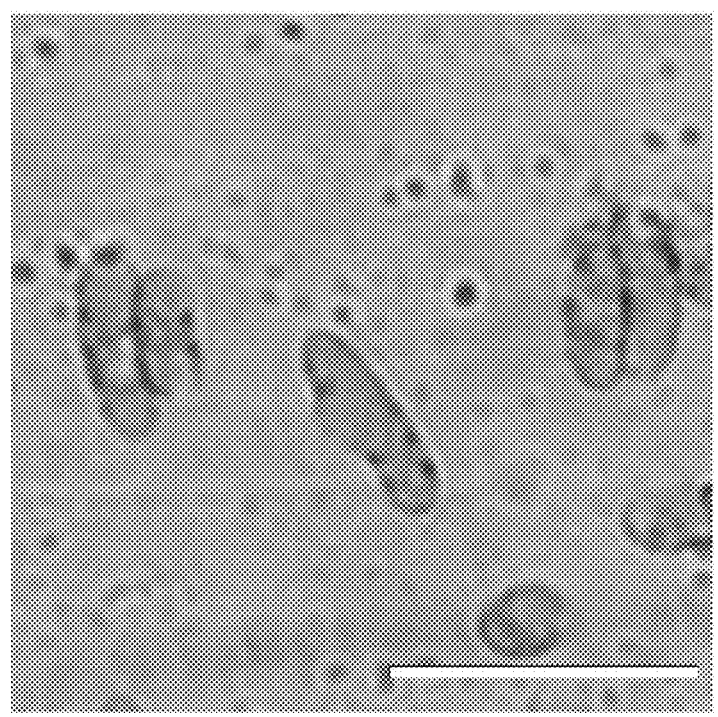
FIG. 8 is a microscope image of an A1386-A2405-double disrupted strain which was cultured (Example 4).

Culture examination using the A1386-A2405-double disrupted strain was conducted under the examination conditions as described in Comparative Example 1. The measurement results of the accumulated PHA percentage and the cell size are listed in Table 1. An image taken by the microscopic cell observation conducted as previously described is shown in FIG. 8.

The results of the culture examination revealed that the cell size of the A1386-A2405-double disrupted strain, as measured under the conditions previously described, was more than 40% above that of the KNK-005 strain which was a parent strain. This means that the A1386 disruption and the A2405 disruption had a synergetic effect or an additive effect on increase in cell size. Additionally, the PHA productivity was comparable to that of the KNK-005 strain.

(Example 5) PHA production by minCD-expressed, A1386-disrupted strain

Figure 9:
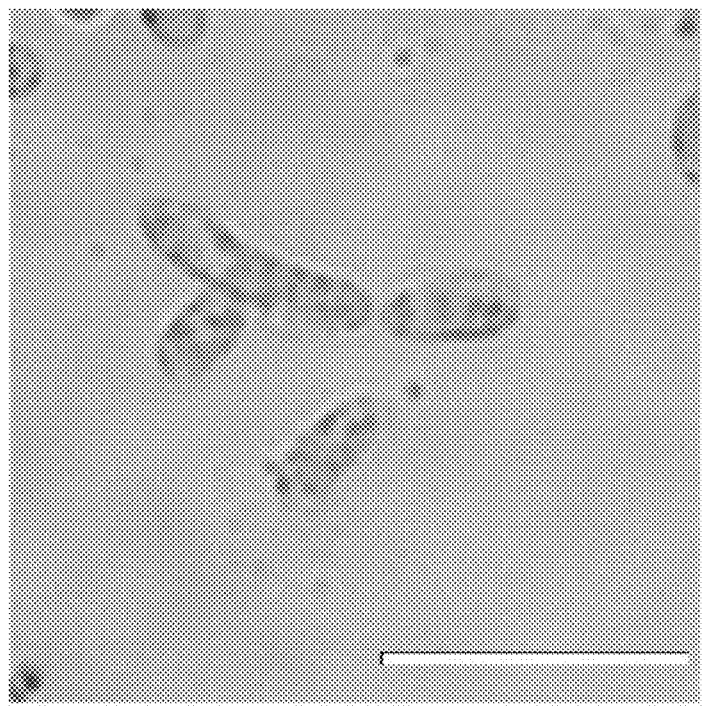
FIG. 9 is a microscope image of a minCD-expressed, A1386-disrupted strain which was cultured (Example 5).

Culture examination using the minCD-expressed, A1386-disrupted strain was conducted under the examination conditions as described in Comparative Example 1. The measurement results of the accumulated PHA percentage and the cell size are listed in Table 1. An image taken by the microscopic cell observation conducted as previously described is shown in FIG. 9.

The results of the culture examination revealed that the cell size of the minCD-expressed, A1386-disrupted strain, as measured under the conditions previously described, was more than 20% above that of the KNK-005 strain which was a parent strain. Additionally, the PHA productivity was comparable to that of the KNK-005 strain.

(Example 6) PHA Production by minCD-Expressed, A2405-Disrupted Strain

Figure 10:
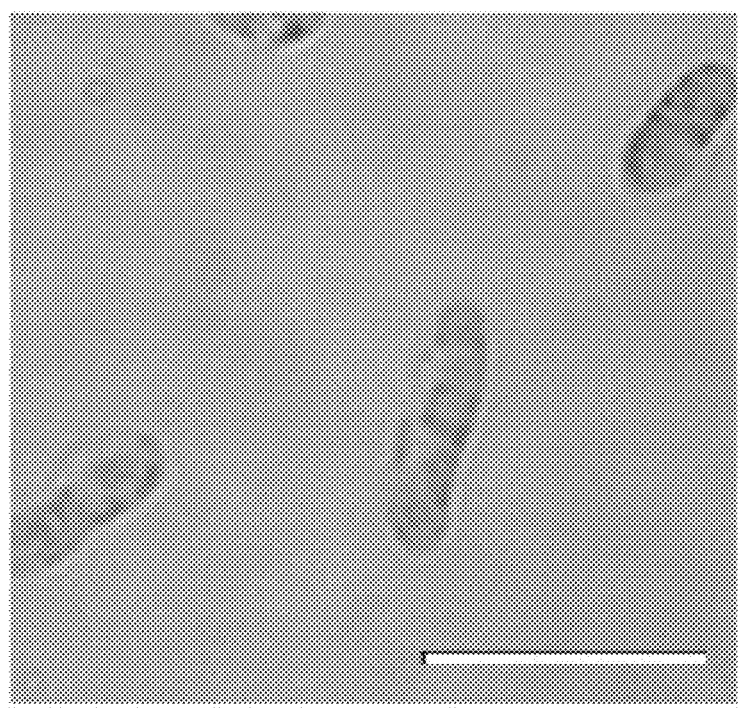
FIG. 10 is a microscope image of a minCD-expressed, A2405-disrupted strain which was cultured (Example 6).

Culture examination using the minCD-expressed, A2405-disrupted strain was conducted under the examination conditions as described in Comparative Example 1. The measurement results of the accumulated PHA percentage and the cell size are listed in Table 1. An image taken by the microscopic cell observation conducted as previously described is shown in FIG. 10.

The results of the culture examination revealed that the cell size of the minCD-expressed, A2405-disrupted strain, as measured under the conditions previously described, was more than 40% above that of the KNK-005 strain which was a parent strain. This means that the A2405 disruption and the minCD expression had a synergetic effect or an additive effect on increase in cell size. Additionally, the PHA productivity was comparable to that of the KNK-005 strain.

(Example 7) PHA Production by minCD-Expressed, A2405-A1386-Disrupted Strain

Figure 11:
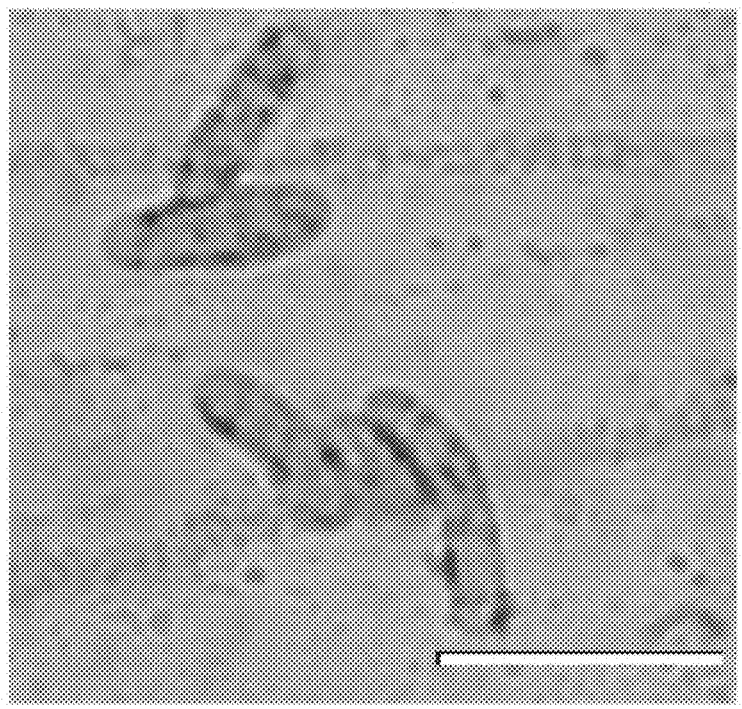
FIG. 11 is a microscope image of a minCD-expressed, A2405-A1386-disrupted strain which was cultured (Example 7).

Culture examination using the minCD-expressed, A2405-A1386-disrupted strain was conducted under the examination conditions as described in Comparative Example 1. The measurement results of the accumulated PHA percentage and the cell size are listed in Table 1. An image taken by the microscopic cell observation conducted as previously described is shown in FIG. 11.

The results of the culture examination revealed that the cell size of the minCD-expressed, A2405-A1386-disrupted strain, as measured under the conditions previously described, was more than 50% above that of the KNK-005 strain which was a parent strain. This means that the A1386 disruption, the A2405 disruption, and the minCD expression had a synergetic effect or an additive effect on increase in cell size. Additionally, the PHA productivity was comparable to that of the KNK-005 strain.

The PHA produced in the culture examinations in Comparative Examples and Examples was found to be PHBH by HPLC analysis.

TABLE 1

| | Strain | Percentage of accumulated PHA to dried microbial bodies (%) | Cell size (μm) |
|---|---|---|---|
| Comp. Example 1 | KNK-005 | 90 | 1.89 |
| Comp. Example 2 | A0597-deletionally disrupted strain | 87 | 1.68 |
| Comp. Example 3 | A0302-deletionally disrupted strain | 87 | 1.45 |
| Comp. Example 4 | A2272-insertionally disrupted strain | 89 | 1.90 |
| Example 1 | A1386-deletionally disrupted strain | 90 | 2.46 |
| Example 2 | A2405-inertionally disrupted strain | 90 | 2.26 |
| Example 3 | A2405-deletionally disrupted strain | 91 | 2.37 |
| Example 4 | A1386-A2405-double disrupted strain | 90 | 2.66 |
| Example 5 | minCD-expressed, A1386-disrupted strain | 88 | 2.32 |
| Example 6 | minCD-expressed, A2405-disrupted strain | 91 | 2.69 |
| Example 7 | minCD-expressed, A2405-A1386-disrupted strain | 90 | 2.86 |

The invention claimed is:

1. A transformed microorganism comprising a polyhydroxyalkanoate synthase gene, wherein expression of an A1386 gene and/or an A2405 gene is reduced as compared to a wild strain of the microorganism,
    wherein the transformed microorganism is *Cupriavidus necator*.

2. The transformed microorganism according to claim 1, wherein the A1386 gene encodes an amino acid sequence that is at least 85% identical to the amino acid sequence of SEQ ID NO: 1.

3. The transformed microorganism according to claim 1, wherein the A2405 gene encodes an amino acid sequence that is at least 85% identical to the amino acid sequence of SEQ ID NO: 2.

4. The transformed microorganism according to claim 1, wherein expression of a minC gene and a minD gene is enhanced as compared to the wild strain of the microorganism.

5. The transformed microorganism according to claim 4, wherein the minC gene encodes an amino acid sequence that is at least 85% identical to the amino acid sequence of SEQ ID NO: 3.

6. The transformed microorganism according to claim 4, wherein the minD gene encodes an amino acid sequence that is at least 85% identical to the amino acid sequence of SEQ ID NO: 4.

7. The transformed microorganism according to claim 4,
    wherein the minC gene encodes an amino acid sequence that is at least 90% identical to the amino acid sequence of SEQ ID NO: 3, and
    the minD gene encodes an amino acid sequence that is at least 90% identical to the amino acid sequence of SEQ ID NO: 4.

8. The transformed microorganism according to claim 4,
    wherein the minC gene encodes an amino acid sequence that is at least 95% identical to the amino acid sequence of SEQ ID NO: 3, and
    the minD gene encodes an amino acid sequence that is at least 95% identical to the amino acid sequence of SEQ ID NO: 4.

9. The transformed microorganism according to claim 1,
    wherein the A1386 gene encodes an amino acid sequence that is at least 90% identical to the amino acid sequence of SEQ ID NO: 1, and
    the A2405 gene encodes an amino acid sequence that is at least 90% identical to the amino acid sequence of SEQ ID NO: 2.

10. The transformed microorganism according to claim 1,
    wherein the A1386 gene encodes an amino acid sequence that is at least 95% identical to the amino acid sequence of SEQ ID NO: 1, and
    the A2405 gene encodes an amino acid sequence that is at least 95% identical to the amino acid sequence of SEQ ID NO: 2.

11. The transformed microorganism according to claim 1, capable of accumulating a polyhydroxyalkanoate in the microorganism cell.

12. A method of producing a polyhydroxyalkanoate, comprising:
    culturing the transformed microorganism according to claim 1 in the presence of a carbon source.

13. The method according to claim 12, wherein the polyhydroxyalkanoate is a copolymer of at least two hydroxyalkanoates.

14. The method according to claim 13, wherein the polyhydroxyalkanoate is a copolymer comprising 3-hydroxyhexanoate as a monomer unit.

15. The method according to claim 14, wherein the polyhydroxyalkanoate is a copolymer of 3-hydroxybutyrate and 3-hydroxyhexanoate.

* * * * *

SEQUENCE LISTING

<160> NUMBER OF SEQ ID NOS: 23

<210> SEQ ID NO 1
<211> LENGTH: 380
<212> TYPE: PRT
<213> ORGANISM: Cupriavidus necator

<400> SEQUENCE: 1

```
Met Ser Met Val Ala Ala Pro Val Ala Glu Ala Thr Lys Ser Ala
1               5                   10                  15

Thr Thr Gln Lys Thr Ser Lys Lys Gln Val Lys Ser Val Asn Ala Glu
            20                  25                  30

Lys Lys Gly Ala Ser Lys Ile Val Ala Lys Ser Ser Arg Ser Gly Lys
                35                  40                  45

Val Ala Lys Arg Glu Ala Ser Ser Thr Arg Lys Val Val Val Leu Lys
        50                  55                  60

Asn Gly Lys Arg His Thr Val Ala Gln Arg Ala Ala Pro Val Arg
65                  70                  75                  80

Ala Ala Phe Thr Pro Ala Lys Pro Ser Leu Gly Glu Ala Met Gly Leu
                85                  90                  95

Arg Asp Thr Asp Asp Ala Leu Ala Leu Arg Ser Ser Val Ala Leu Val
                100                 105                 110

Met Asp Gln Asn Ser Asn Glu Val Leu Phe Gln Lys Asn Ala Ser Ala
                115                 120                 125

Val Leu Pro Ile Ala Ser Ile Thr Lys Leu Met Thr Ala Leu Val Val
        130                 135                 140

Met Asp Ala Arg Leu Pro Met Asp Glu Val Leu Thr Ile Ser Glu Glu
145                 150                 155                 160

Asp Arg Asp Thr Glu Lys His Ser Gly Ser Arg Leu Arg Phe Gly Thr
                165                 170                 175

Gln Leu Thr Arg Gln Glu Leu Leu Leu Ala Leu Met Ser Ser Glu
                180                 185                 190

Asn Arg Ala Ala Ser Ala Leu Gly Arg Asn Tyr Pro Gly Gly Leu Pro
                195                 200                 205

Ala Phe Val Gln Ala Met Asn Arg Lys Ala Arg Glu Leu Gly Met Asn
        210                 215                 220

Asp Ser His Phe Val Asp Ser Ser Gly Leu Ser Ser Ser Asn Val Ser
225                 230                 235                 240

Ser Ala Thr Asp Leu Val Arg Met Val Asn Ala Ala Tyr Arg Asn Pro
                245                 250                 255

Thr Ile Arg Glu Phe Ser Thr Gln Thr Glu His Glu Val Asn Val Leu
                260                 265                 270

Gly Arg Thr Gln His Tyr Val Ser Thr Asn Arg Leu Val Arg Gly Gly
                275                 280                 285

Asn Trp Glu Ile Gly Leu Gln Lys Thr Gly Phe Ile Ser Glu Ala Gly
        290                 295                 300

Gln Cys Leu Val Met Gln Ala Lys Val Gln Gly Arg Asn Val Val Met
305                 310                 315                 320

Val Phe Leu Asp Ser Ala Gly Lys Leu Ser Arg Phe Ala Asp Ala Asn
                325                 330                 335

Arg Val Lys Asp Trp Leu Glu His Ala Pro Ser Pro Ser Ser Pro Gln
                340                 345                 350

Arg Gly Phe Pro Ser Ser Pro Asn Leu Thr Gln Ala Pro Gly Gly Ala
                355                 360                 365
```

```
                His Ala Ile Leu Ala Ser Gln Ser Arg Gly Ile
                    370                 375                 380
```

<210> SEQ ID NO 2
<211> LENGTH: 226
<212> TYPE: PRT
<213> ORGANISM: Cupriavidus necator

<400> SEQUENCE: 2

```
Met Gln Arg Ser Val Leu His Ser Leu Ala Arg Ala Val Gly Ile
1               5                   10                  15

Ala Ile Val Cys Gly Ala Thr Val Ser Asn Gly Val Leu Ala Asp Thr
                20                  25                  30

Val Phe Lys Asp Ala Asp Ala Arg Ile Asp Ala Thr Ala His Ala Ala
                35                  40                  45

Asp Ser His Ala Glu Gly Lys Arg Gly Leu Leu Ser Val Val Asn
                50                  55                  60

Ser Thr Ser Asn Val Ala Ser Lys Ala Gly Asp Leu Val Met Asn Ala
65                  70                  75                  80

Leu Gly Leu Ile Gly Val Arg Tyr Arg Phe Gly Gly Asn Ser Pro Glu
                85                  90                  95

Ser Gly Leu Asp Cys Ser Gly Phe Val Arg Tyr Val Phe Gln Asp Thr
                100                 105                 110

Phe Gly Phe Met Leu Pro Arg Arg Ser Val Glu Ile Ser Arg Val Gly
                115                 120                 125

Thr Thr Val Ala Ala Thr Asp Leu Arg Pro Gly Asp Leu Val Phe Phe
                130                 135                 140

Asn Thr Met Arg Gln Thr Phe Ser His Val Gly Ile Tyr Ile Gly Asp
145                 150                 155                 160

Asn Lys Phe Val His Ala Pro Ser Thr Gly Ser Lys Ile Arg Val Asp
                165                 170                 175

Asp Met Arg Ala Ser Tyr Trp Val Thr Arg Tyr Asn Gly Ala Arg Arg
                180                 185                 190

Ile Glu Asp Gly Lys Glu Gly Gly Ala Asp Gly Leu Gly Asp Met Val
                195                 200                 205

Glu Thr Leu Lys Arg Tyr Asp Pro Lys Val Val Arg Ala Ser Met Tyr
                210                 215                 220

Gly Gly
225
```

<210> SEQ ID NO 3
<211> LENGTH: 270
<212> TYPE: PRT
<213> ORGANISM: Cupriavidus necator

<400> SEQUENCE: 3

```
Met Ser Gln Lys Lys Ser Pro Arg Phe Glu Leu Arg Ser Gly Asn Val
1               5                   10                  15

Asp Ala Leu Leu Ala Leu Gln Thr Ala Asp Met Ala Ala Leu Arg
                20                  25                  30

Asp Asp Leu Leu Ala Arg Phe Glu Ala Thr Pro Asp Phe Phe Ser Asn
                35                  40                  45

Asp Val Ile Ala Leu Asp Leu Arg Ala Leu Asp Asp Ser Glu Val
                50                  55                  60

Ala Leu Gly Thr Val Ile Glu Thr Leu Ala Thr Leu Arg Ala Arg Ala
65                  70                  75                  80
```

Ile Gly Val Val Ala Arg Pro Gly Gln Arg Glu Trp Ala Glu Arg Phe
                85                  90                  95

Gly Leu Pro Leu Leu Asp Ser Gln Ala Arg Arg Gly Ser Gly Ala Asp
            100                 105                 110

Arg Ala Thr Asp Arg Ala Ala Glu Ala Arg Ala Ala Ala Ala Ala Glu
            115                 120                 125

Gln Ala Ala Ala Asp Gln Ala Ala Arg Glu Glu Ser Ile Arg Ala Ala
        130                 135                 140

Ala Gln Ala Thr Thr Asp Ala Ala Val Ala Ala Ile Arg Gln Thr
145                 150                 155                 160

Gln Thr Met Leu Ile Asp Lys Pro Leu Arg Ser Gly Gln Gln Val Tyr
                165                 170                 175

Ala Gln Gly Asp Val Val Ile Leu Asp Val Val Ser Tyr Gly Ala Glu
            180                 185                 190

Val Ile Ala Glu Gly Asn Ile His Ile Tyr Ala Pro Leu Arg Gly Arg
            195                 200                 205

Ala Leu Ala Gly Val Lys Gly Asn Thr Gly Ala Arg Ile Phe Ser Thr
        210                 215                 220

Cys Met Glu Pro Glu Leu Ile Ser Ile Ala Gly Ile Tyr Arg Thr Ala
225                 230                 235                 240

Glu Gln Thr Leu Pro Ala Asp Val Leu Gly Lys Thr Ala Gln Val Arg
                245                 250                 255

Leu Ala Asp Glu Lys Leu Ile Leu Glu Ala Leu Arg Leu Lys
            260                 265                 270

<210> SEQ ID NO 4
<211> LENGTH: 271
<212> TYPE: PRT
<213> ORGANISM: Cupriavidus necator

<400> SEQUENCE: 4

Met Ala Lys Ile Ile Val Val Thr Ser Gly Lys Gly Gly Val Gly Lys
1               5                   10                  15

Thr Thr Thr Ser Ala Ser Phe Ala Ala Gly Leu Ala Leu Arg Gly His
                20                  25                  30

Lys Thr Ala Val Ile Asp Phe Asp Val Gly Leu Arg Asn Leu Asp Leu
            35                  40                  45

Ile Met Gly Cys Glu Arg Arg Val Val Tyr Asp Leu Ile Asn Val Val
        50                  55                  60

Gln Gly Glu Ala Asn Leu Arg Gln Ala Leu Ile Lys Asp Lys Lys Cys
65                  70                  75                  80

Glu Asn Leu Phe Ile Leu Pro Ala Ser Gln Thr Arg Asp Lys Asp Ala
                85                  90                  95

Leu Thr Arg Glu Gly Val Glu Lys Val Ile Asn Gly Leu Ile Glu Met
            100                 105                 110

Asp Phe Glu Phe Ile Ile Cys Asp Ser Pro Ala Gly Ile Glu Ser Gly
            115                 120                 125

Ala Leu Met Ala Met Tyr Phe Ala Asp Glu Ala Leu Ile Val Thr Asn
        130                 135                 140

Pro Glu Val Ser Ser Val Arg Asp Ser Asp Arg Ile Leu Gly Ile Leu
145                 150                 155                 160

Ala Ser Lys Thr Lys Arg Ala Ser Glu Gly Gly Asp Pro Ile Lys Glu
                165                 170                 175

His Leu Leu Ile Thr Arg Tyr Asn Pro Lys Arg Val His Gly Gly Glu
            180                 185                 190

```
Met Leu Ser Leu Thr Asp Ile Gln Glu Ile Leu Arg Ile Lys Leu Ile
        195                 200                 205

Gly Val Val Pro Glu Ser Glu Ala Val Leu His Ala Ser Asn Gln Gly
    210                 215                 220

Thr Pro Ala Ile His Leu Glu Gly Ser Asp Val Ala Asp Ala Tyr Gly
225                 230                 235                 240

Asp Val Val Asp Arg Phe Leu Gly Lys Asp Lys Pro Met Arg Phe Thr
                245                 250                 255

Asp Tyr Gln Lys Pro Gly Leu Leu Ser Arg Ile Phe Gly Asn Lys
        260                 265                 270

<210> SEQ ID NO 5
<211> LENGTH: 589
<212> TYPE: PRT
<213> ORGANISM: Cupriavidus necator

<400> SEQUENCE: 5

Met Ala Thr Gly Lys Gly Ala Ala Ser Thr Gln Glu Gly Lys Ser
1               5                   10                  15

Gln Pro Phe Lys Val Thr Pro Gly Pro Phe Asp Pro Ala Thr Trp Leu
            20                  25                  30

Glu Trp Ser Arg Gln Trp Gln Gly Thr Glu Gly Asn Gly His Ala Ala
        35                  40                  45

Ala Ser Gly Ile Pro Gly Leu Asp Ala Leu Ala Gly Val Lys Ile Ala
    50                  55                  60

Pro Ala Gln Leu Gly Asp Ile Gln Gln Arg Tyr Met Lys Asp Phe Ser
65                  70                  75                  80

Ala Leu Trp Gln Ala Met Ala Glu Gly Lys Ala Glu Ala Thr Gly Pro
                85                  90                  95

Leu His Asp Arg Arg Phe Ala Gly Asp Ala Trp Arg Thr Asn Leu Pro
            100                 105                 110

Tyr Arg Phe Ala Ala Ala Phe Tyr Leu Leu Asn Ala Arg Ala Leu Thr
        115                 120                 125

Glu Leu Ala Asp Ala Val Glu Ala Asp Ala Lys Thr Arg Gln Arg Ile
    130                 135                 140

Arg Phe Ala Ile Ser Gln Trp Val Asp Ala Met Ser Pro Ala Asn Phe
145                 150                 155                 160

Leu Ala Thr Asn Pro Glu Ala Gln Arg Leu Leu Ile Glu Ser Gly Gly
                165                 170                 175

Glu Ser Leu Arg Ala Gly Val Arg Asn Met Met Glu Asp Leu Thr Arg
            180                 185                 190

Gly Lys Ile Ser Gln Thr Asp Glu Ser Ala Phe Glu Val Gly Arg Asn
        195                 200                 205

Val Ala Val Thr Glu Gly Ala Val Val Phe Glu Asn Glu Tyr Phe Gln
    210                 215                 220

Leu Leu Gln Tyr Lys Pro Leu Thr Asp Lys Val His Ala Arg Pro Leu
225                 230                 235                 240

Leu Met Val Pro Pro Cys Ile Asn Lys Tyr Tyr Ile Leu Asp Leu Gln
                245                 250                 255

Pro Glu Ser Ser Leu Val Arg His Val Val Glu Gln Gly His Thr Val
            260                 265                 270

Phe Leu Val Ser Trp Arg Asn Pro Asp Ala Ser Met Ala Gly Ser Thr
        275                 280                 285

Trp Asp Asp Tyr Ile Glu His Ala Ala Ile Arg Ala Ile Glu Val Ala
```

Arg Asp Ile Ser Gly Gln Asp Lys Ile Asn Val Leu Gly Phe Cys Val
305                 310                 315                 320

Gly Gly Thr Ile Val Ser Thr Ala Leu Ala Val Leu Ala Ala Arg Gly
                325                 330                 335

Glu His Pro Ala Ala Ser Val Thr Leu Leu Thr Thr Leu Leu Asp Phe
                340                 345                 350

Ala Asp Thr Gly Ile Leu Asp Val Phe Val Asp Glu Gly His Val Gln
                355                 360                 365

Leu Arg Glu Ala Thr Leu Gly Gly Ala Gly Ala Pro Cys Ala Leu
    370                 375                 380

Leu Arg Gly Leu Glu Leu Ala Asn Thr Phe Ser Phe Leu Arg Pro Asn
385                 390                 395                 400

Asp Leu Val Trp Asn Tyr Val Val Asp Asn Tyr Leu Lys Gly Asn Thr
                405                 410                 415

Pro Val Pro Phe Asp Leu Leu Phe Trp Asn Gly Asp Ala Thr Asn Leu
                420                 425                 430

Pro Gly Pro Trp Tyr Cys Trp Tyr Leu Arg His Thr Tyr Leu Gln Asn
                435                 440                 445

Glu Leu Lys Val Pro Gly Lys Leu Thr Val Cys Gly Val Pro Val Asp
    450                 455                 460

Leu Ala Ser Ile Asp Val Pro Thr Tyr Ile Tyr Gly Ser Arg Glu Asp
465                 470                 475                 480

His Ile Val Pro Trp Thr Ala Ala Tyr Ala Ser Thr Ala Leu Leu Ala
                485                 490                 495

Asn Lys Leu Arg Phe Val Leu Gly Ala Ser Gly His Ile Ala Gly Val
                500                 505                 510

Ile Asn Pro Pro Ala Lys Asn Lys Arg Ser His Trp Thr Asn Asp Ala
                515                 520                 525

Leu Pro Glu Ser Pro Gln Gln Trp Leu Ala Gly Ala Ile Glu His His
                530                 535                 540

Gly Ser Trp Trp Pro Asp Trp Thr Ala Trp Leu Ala Gly Gln Ala Gly
545                 550                 555                 560

Ala Lys Arg Ala Ala Pro Ala Asn Tyr Gly Asn Ala Arg Tyr Arg Ala
                565                 570                 575

Ile Glu Pro Ala Pro Gly Arg Tyr Val Lys Ala Lys Ala
                580                 585

<210> SEQ ID NO 6
<211> LENGTH: 594
<212> TYPE: PRT
<213> ORGANISM: Aeromonas caviae

<400> SEQUENCE: 6

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
                20                  25                  30

Gln Ala Leu Leu Gln Thr Asn Leu Asp Asp Leu Gly Gln Val Leu Glu
            35                  40                  45

Gln Gly Ser Gln Gln Pro Trp Gln Leu Ile Gln Ala Gln Met Asn Trp
        50                  55                  60

Trp Gln Asp Gln Leu Lys Leu Met Gln His Thr Leu Leu Lys Ser Ala
65                  70                  75                  80

```
Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Asn Ala Met Ala Pro Ser Asn Phe Leu Ala Thr Asn
145                 150                 155                 160

Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270

Phe Met Ile Ser Trp Arg Asn Pro Gly Val Ala Gln Ala Gln Ile Asp
        275                 280                 285

Leu Asp Asp Tyr Val Val Asp Gly Val Ile Ala Ala Leu Asp Gly Val
    290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
            340                 345                 350

Phe Ser Gln Pro Gly Glu Leu Gly Ile Phe Ile His Glu Pro Ile Ile
        355                 360                 365

Ala Ala Leu Glu Ala Gln Asn Glu Ala Lys Gly Ile Met Asp Gly Arg
    370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                405                 410                 415

Asp Leu Leu His Trp Asn Ser Asp Ser Thr Asn Val Ala Gly Lys Thr
            420                 425                 430

His Asn Ser Leu Leu Arg Arg Leu Tyr Leu Glu Asn Gln Leu Val Lys
        435                 440                 445

Gly Glu Leu Lys Ile Arg Asn Thr Arg Ile Asp Leu Gly Lys Val Lys
    450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                485                 490                 495

Leu Leu Ala Glu Ser Gly His Ile Ala Gly Ile Ile Asn Pro Pro Ala
```

```
                    500                 505                 510
Ala Asn Lys Tyr Gly Phe Trp His Asn Gly Ala Glu Ala Glu Ser Pro
            515                 520                 525

Glu Ser Trp Leu Ala Gly Ala Thr His Gln Gly Gly Ser Trp Trp Pro
        530                 535                 540

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Ala Pro Gly His Tyr
                565                 570                 575

Val Lys Val Arg Leu Asn Pro Val Phe Ala Cys Pro Thr Glu Glu Asp
            580                 585                 590

Ala Ala

<210> SEQ ID NO 7
<211> LENGTH: 594
<212> TYPE: PRT
<213> ORGANISM: Aeromonas caviae

<400> SEQUENCE: 7

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Ser Ala Met Ala Pro Ser Asn Phe Leu Ala Thr Asn
145                 150                 155                 160

Pro Glu Leu Leu Lys Leu Thr Leu Glu Ser Gly Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270

Phe Met Ile Ser Trp Arg Asn Pro Gly Val Ala Gln Ala Gln Ile Asp
```

```
              275                 280                 285
Leu Asp Asp Tyr Val Val Asp Gly Val Ile Ala Ala Leu Asp Gly Val
    290                 295                 300
Glu Ala Ala Thr Gly Glu Arg Glu Val His Gly Ile Gly Tyr Cys Ile
305                 310                 315                 320
Gly Gly Thr Ala Leu Ser Leu Ala Met Gly Trp Leu Ala Ala Arg
                325                 330                 335
Gln Lys Gln Arg Val Arg Thr Ala Thr Leu Phe Thr Thr Leu Leu Asp
            340                 345                 350
Phe Ser Gln Pro Gly Glu Leu Gly Ile Phe Ile His Glu Pro Ile Ile
                355                 360                 365
Ala Ala Leu Glu Ala Gln Asn Glu Ala Lys Gly Ile Met Asp Gly Arg
        370                 375                 380
Gln Leu Ala Val Ser Phe Ser Leu Leu Arg Glu Asn Ser Leu Tyr Trp
385                 390                 395                 400
Asn Tyr Tyr Ile Asp Ser Tyr Leu Lys Gly Gln Ser Pro Val Ala Phe
                405                 410                 415
Asp Leu Leu His Trp Asn Ser Asp Ser Thr Asn Val Ala Gly Lys Thr
            420                 425                 430
His Asn Ser Leu Leu Arg Arg Leu Tyr Leu Glu Asn Gln Leu Val Lys
        435                 440                 445
Gly Glu Leu Lys Ile Arg Asn Thr Arg Ile Asp Leu Gly Lys Val Lys
    450                 455                 460
Thr Pro Val Leu Leu Val Ser Ala Val Asp Asp His Ile Ala Leu Trp
465                 470                 475                 480
Gln Gly Thr Trp Gln Gly Met Lys Leu Phe Gly Gly Glu Gln Arg Phe
                485                 490                 495
Leu Leu Ala Glu Ser Gly His Ile Ala Gly Ile Ile Asn Pro Pro Ala
            500                 505                 510
Ala Asn Lys Tyr Gly Phe Trp His Asn Gly Ala Glu Ala Glu Ser Pro
        515                 520                 525
Glu Ser Trp Leu Ala Gly Ala Thr His Gln Gly Gly Ser Trp Trp Pro
    530                 535                 540
Glu Met Met Gly Phe Ile Gln Asn Arg Asp Glu Gly Ser Glu Pro Val
545                 550                 555                 560
Pro Ala Arg Val Pro Glu Glu Gly Leu Ala Pro Ala Pro Gly His Tyr
                565                 570                 575
Val Lys Val Arg Leu Asn Pro Val Phe Ala Cys Pro Thr Glu Glu Asp
            580                 585                 590
Ala Ala

<210> SEQ ID NO 8
<211> LENGTH: 567
<212> TYPE: PRT
<213> ORGANISM: Chromobacterium sp.

<400> SEQUENCE: 8

Met Gln Gln Phe Val Asn Ser Leu Ser Leu Gly Gln Asp Gln Ser Asp
1               5                   10                  15
Ala Pro His Pro Leu Thr Gly Ala Trp Ser Gln Leu Met Ser Gln Thr
                20                  25                  30
Asn Gln Leu Leu Gln Leu Gln Ser Ser Leu Tyr Gln Gln Leu Gly
        35                  40                  45
Leu Trp Thr Gln Phe Leu Gly Gln Thr Ala Gly Asn Asp Ala Ser Ala
```

```
                    50                  55                  60
        Pro Ser Ala Lys Pro Ser Asp Arg Arg Phe Ala Ser Pro Glu Trp Asp
        65                  70                  75                  80

Glu His Pro Phe Tyr Ser Phe Leu Lys Gln Ser Tyr Leu Gln Thr Ser
                            85                  90                  95

Lys Trp Met Met Glu Leu Val Asp Lys Thr Gln Ile Asp Glu Ser Ala
                        100                 105                 110

Lys Asp Lys Leu Ser Phe Ala Thr Arg Gln Tyr Leu Asp Ala Met Ala
                    115                 120                 125

Pro Ser Asn Phe Met Leu Thr Asn Pro Asp Val Val Lys Arg Ala Ile
                130                 135                 140

Glu Thr Gln Gly Glu Ser Leu Val Glu Gly Met Lys Asn Met Met Glu
        145                 150                 155                 160

Asp Ile Gln Lys Gly His Ile Ser Met Ser Asp Glu Ser Lys Phe Gln
                            165                 170                 175

Ile Gly Lys Asn Leu Val Val Thr Pro Gly Glu Val Val Phe Arg Asn
                        180                 185                 190

Glu Leu Ile Glu Leu Ile Gln Tyr Thr Pro Thr Thr Glu Lys Val His
                    195                 200                 205

Glu Lys Pro Leu Leu Phe Val Pro Pro Cys Ile Asn Lys Tyr Tyr Leu
                210                 215                 220

Met Asp Leu Gln Pro Asp Asn Ser Met Val Arg His Phe Val Gly Gln
        225                 230                 235                 240

Gly Tyr Arg Val Phe Leu Val Ser Trp Arg Ser Ala Val Pro Glu Met
                            245                 250                 255

Lys Asn Phe Thr Trp Glu Thr Tyr Ile Glu Lys Gly Val Phe Ala Ala
                        260                 265                 270

Ala Glu Ala Val Gln Lys Ile Thr Lys Gln Pro Thr Met Asn Ala Leu
                    275                 280                 285

Gly Phe Cys Val Gly Gly Val Ile Leu Thr Thr Ala Leu Cys Val Ala
                290                 295                 300

Gln Ala Lys Gly Leu Lys Tyr Phe Asp Ser Ala Thr Phe Met Thr Ser
        305                 310                 315                 320

Leu Ile Asp His Ala Glu Pro Gly Glu Ile Ser Phe Phe Ile Asp Glu
                            325                 330                 335

Ala Leu Val Ala Ser Arg Glu Ala Lys Met Ala Ala Gly Gly Ile Ile
                        340                 345                 350

Ser Gly Lys Glu Ile Gly Arg Thr Phe Ala Ser Leu Arg Ala Asn Asp
                    355                 360                 365

Leu Val Trp Asn Tyr Val Val Asn Asn Tyr Leu Leu Gly Lys Thr Pro
                370                 375                 380

Ala Pro Phe Asp Leu Leu Tyr Trp Asn Asn Asp Ala Val Asp Leu Pro
        385                 390                 395                 400

Leu Pro Met His Thr Phe Met Leu Arg Gln Phe Tyr Ile Asn Asn Ala
                            405                 410                 415

Leu Ile Thr Pro Gly Ala Ile Thr Leu Cys Gly Val Pro Ile Asp Ile
                        420                 425                 430

Ser Lys Ile Asp Ile Pro Val Tyr Met Phe Ala Ala Arg Glu Asp His
                    435                 440                 445

Ile Val Leu Trp Ser Ser Ala Tyr Ser Gly Leu Lys Tyr Leu Ser Gly
                450                 455                 460

Thr Pro Ser Arg Arg Phe Val Leu Gly Ala Ser Gly His Ile Ala Gly
        465                 470                 475                 480
```

```
Ser Ile Asn Pro Val Thr Lys Asp Lys Arg Asn Tyr Trp Thr Asn Glu
                485                 490                 495

Gln Leu Pro Val Asn Pro Glu Glu Trp Leu Glu Gly Ala Gln Ser His
            500                 505                 510

Pro Gly Ser Trp Trp Lys Asp Trp Asp Ala Trp Leu Ala Pro Gln Ser
        515                 520                 525

Gly Lys Gln Val Pro Ala Pro Lys Met Leu Gly Ser Lys Glu Phe Pro
    530                 535                 540

Pro Leu Gln Pro Ala Pro Gly Ser Tyr Val Leu Ala Lys Ala Met Pro
545                 550                 555                 560

Pro Val Ala Ala Ala Leu Asn
                565

<210> SEQ ID NO 9
<211> LENGTH: 559
<212> TYPE: PRT
<213> ORGANISM: Pseudomonas sp.

<400> SEQUENCE: 9

Met Ser Asn Lys Asn Ser Asp Asp Leu Asn Arg Gln Ala Ser Glu Asn
1               5                   10                  15

Thr Leu Gly Leu Asn Pro Val Ile Gly Leu Arg Gly Lys Asp Leu Leu
            20                  25                  30

Thr Ser Ala Arg Met Val Leu Thr Gln Ala Ile Lys Gln Pro Ile His
        35                  40                  45

Ser Val Lys His Val Ala His Phe Gly Ile Glu Leu Lys Asn Val Met
    50                  55                  60

Phe Gly Lys Ser Lys Leu Gln Pro Glu Ser Asp Asp Arg Arg Phe Asn
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Gly Asn Ser Lys
            100                 105                 110

Leu Ser Glu Gln Asp Ile Asn Arg Ala His Phe Val Ile Thr Leu Met
        115                 120                 125

Thr Glu Ala Met Ala Pro Thr Asn Ser Ala Ala Asn Pro Ala Ala Val
    130                 135                 140

Lys Arg Phe Phe Glu Thr Gly Gly Lys Ser Leu Leu Asp Gly Leu Thr
145                 150                 155                 160

His Leu Ala Lys Asp Leu Val Asn Asn Gly Gly Met Pro Ser Gln Val
                165                 170                 175

Asp Met Gly Ala Phe Glu Val Gly Lys Ser Leu Gly Thr Thr Glu Gly
            180                 185                 190

Ala Val Val Phe Arg Asn Asp Val Leu Glu Leu Ile Gln Tyr Arg Pro
        195                 200                 205

Thr Thr Glu Gln Val His Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Ser Asn Asn Gln Gln Thr Phe Ile Val Ser Trp Arg
                245                 250                 255

Asn Pro Thr Lys Ala Gln Arg Glu Trp Gly Leu Ser Thr Tyr Ile Asp
            260                 265                 270

Ala Leu Lys Glu Ala Val Asp Val Val Ser Ala Ile Thr Gly Ser Lys
```

```
                275                 280                 285
Asp Ile Asn Met Leu Gly Ala Cys Ser Gly Gly Ile Thr Cys Thr Ala
    290                 295                 300
Leu Leu Gly His Tyr Ala Ala Leu Gly Glu Lys Lys Val Asn Ala Leu
305                 310                 315                 320
Thr Leu Leu Val Ser Val Leu Asp Thr Thr Leu Asp Ser Gln Val Ala
                325                 330                 335
Leu Phe Val Asp Glu Lys Thr Leu Glu Ala Ala Lys Arg His Ser Tyr
            340                 345                 350
Gln Ala Gly Val Leu Glu Gly Arg Asp Met Ala Lys Val Phe Ala Trp
        355                 360                 365
Met Arg Pro Asn Asp Leu Ile Trp Asn Tyr Trp Val Asn Asn Tyr Leu
    370                 375                 380
Leu Gly Asn Glu Pro Pro Val Phe Asp Ile Leu Phe Trp Asn Asn Asp
385                 390                 395                 400
Thr Thr Arg Leu Pro Ala Ala Phe His Gly Asp Leu Ile Glu Met Phe
                405                 410                 415
Lys Asn Asn Pro Leu Val Arg Ala Asn Ala Leu Glu Val Ser Gly Thr
            420                 425                 430
Pro Ile Asp Leu Lys Gln Val Thr Ala Asp Ile Tyr Ser Leu Ala Gly
        435                 440                 445
Thr Asn Asp His Ile Thr Pro Trp Lys Ser Cys Tyr Lys Ser Ala Gln
    450                 455                 460
Leu Phe Gly Gly Lys Val Glu Phe Val Leu Ser Ser Gly His Ile
465                 470                 475                 480
Gln Ser Ile Leu Asn Pro Pro Gly Asn Pro Lys Ser Arg Tyr Met Thr
                485                 490                 495
Ser Thr Asp Met Pro Ala Thr Ala Asn Glu Trp Gln Glu Asn Ser Thr
            500                 505                 510
Lys His Thr Asp Ser Trp Trp Leu His Trp Gln Ala Trp Gln Ala Glu
        515                 520                 525
Arg Ser Gly Lys Leu Lys Lys Ser Pro Thr Ser Leu Gly Asn Lys Ala
    530                 535                 540
Tyr Pro Ser Gly Glu Ala Ala Pro Gly Thr Tyr Val His Glu Arg
545                 550                 555

<210> SEQ ID NO 10
<211> LENGTH: 29
<212> TYPE: DNA
<213> ORGANISM: Artificial Sequence
<220> FEATURE:
<223> OTHER INFORMATION: Synthetic DNA

<400> SEQUENCE: 10
ttgacaatta atcatccggc tcgtataat                                    29

<210> SEQ ID NO 11
<211> LENGTH: 30
<212> TYPE: DNA
<213> ORGANISM: Escherichia coli

<400> SEQUENCE: 11
tttacacttt atgcttccgg ctcgtataat                                   30

<210> SEQ ID NO 12
<211> LENGTH: 30
<212> TYPE: DNA
```

<213> ORGANISM: Escherichia coli

<400> SEQUENCE: 12
ttgacaatta atcatcgaac tagttaacta                                    30

<210> SEQ ID NO 13
<211> LENGTH: 30
<212> TYPE: DNA
<213> ORGANISM: Escherichia coli

<400> SEQUENCE: 13
tttacacttt atgcttccgg ctcgtatgtt                                    30

<210> SEQ ID NO 14
<211> LENGTH: 30
<212> TYPE: DNA
<213> ORGANISM: Cupriavidus necator

<400> SEQUENCE: 14
ttgacagcgc gtgcgttgca aggcaacaat                                    30

<210> SEQ ID NO 15
<211> LENGTH: 231
<212> TYPE: DNA
<213> ORGANISM: Cupriavidus necator

<400> SEQUENCE: 15
tacgccgccc cctgaccagg aacgccgggc cagtcccggc gttttttat tctatagcgc    60 aattaaccgc cgtcatattg cgtcaccatg attgccggat ggccgcggcg atcccttgct  120
ggaggccggt tccaagaaga tttaaagatg tcacggaatt gtcatacagg gagcatagag  180
ttcgtcttgt caaaaatttg tcattcccaa ccaatgttct ctggaggaca t           231

<210> SEQ ID NO 16
<211> LENGTH: 17
<212> TYPE: DNA
<213> ORGANISM: Cupriavidus necator

<400> SEQUENCE: 16
agagagacaa tcaaatc                                                  17

<210> SEQ ID NO 17
<211> LENGTH: 890
<212> TYPE: DNA
<213> ORGANISM: Artificial Sequence
<220> FEATURE:
<223> OTHER INFORMATION: Synthetic DNA

<400> SEQUENCE: 17
agtgaattcg gatttaaatt gcatgtgcag ctgtccggcg acctgggcgc cggcaagacc    60
acgctgacgc gcacgatcct gcgcgcgctc ggccatgcgg gcaaggtccg cagccccacc   120
tacacgctgt gcgagcccta cgaggtggcc cgcgccgacg gctcgccgct gaccgtctac   180
cacttcgacc tgtaccgctt tgccgatccc gaagagtgga tcgacgcggg ttttcgcgac   240
tgcttcgccg aaccggcctt caacctggtc gagtggccgg aaaaggccgg ccgcctgctc   300
ggggaaccgg atctccatat gttgctccaa tcggacatgg ccggggcgga tgatgccggc   360
gagcggcgga tcgcgacgat gcgcgcctat actcacactg gacttaccct gctgaacgca   420
tgctgagtct ggcgggcaca aaaaaaccgg ggcatgcccc ggttttttca tggctgcgtg   480
cctcaggccc gcgccgcggc ctggtcctcc tgcaaggcat cgcggtcggc atagcgcgac   540

```
gcgatcaccg agcacacgat cagctgcagc tggtgataga ccatcagcgg cagcaccagc    600
aggcccagcg ccggatggcc ggcaaacagg atcttggcca tcgggatgcc gttggccagg    660
ctcttcttgg agccgcagaa caccgccgtg atctcgtcct cgacagagaa gccaaggcgg    720
cgcgcggtca gcgtggtaaa gcccagcacc acgaacagca gcaccgcggc gatcagcatc    780
actgcgccga tggtctgcca ctggtactgg tgccacaggc cctgggcggt ggcatcgcag    840
aatgaggaat agacgatcag cacgatcacg catttaaatg gatagctcgg               890

<210> SEQ ID NO 18
<211> LENGTH: 769
<212> TYPE: DNA
<213> ORGANISM: Artificial Sequence
<220> FEATURE:
<223> OTHER INFORMATION: Synthetic DNA

<400> SEQUENCE: 18
ccgagctatc catttaaatg gacgaccttc accatcggat gcgaagtcag cgcccgatac     60
aagtcgtcga gctgctcgcg gctggtgacc cacaccgtca cggtcaggcc caggtagttg    120
ccgccgctgg aggggcgcat ttccatcttg ccggcgtgga agtcgggatc gaactcctgc    180
accagcgtga cgatggcctc ggcaaagccg tcctgcatcg cgcccatcac cttgatggga    240
aagtggctgg ggtattcgat cagcgactgc tccggcggga gtcgcccggc ttgttgctg    300 ccttgcttgt cggttgtcat gtcggattct ccggcacgaa accggcgcgc gcatggcgc    360 gccggcttac gcgcattcag ggtttctgtt ttccgacagt aagaaggtgg cgcggggatg    420
gtccgggtgg cggcgtgccg gcctcaccgg tcccacgcat tgacgacgag ctgcttgatc    480
aggtgcagct tgcggtgaaa gaaatggtcg gcgccgggga tcacgatcac cggcagctcc    540
tgcgggcggg cccagtcgaa cacgctggcc agcggcacgg tgtcgtcctg ttcgccatgg    600
atcacgatgg tgtcggccgg cacctcggct acctgccagc ggctggcggc ggtgcccacc    660
agcaccaggc gctgcgcggg cgtgccggcc tcggccaggc ggcgcgccac gtgggtggtg    720
acgaagctgc cgaacgagaa cccgcccatg atttaaatcc gaattcact                769

<210> SEQ ID NO 19
<211> LENGTH: 956
<212> TYPE: DNA
<213> ORGANISM: Artificial Sequence
<220> FEATURE:
<223> OTHER INFORMATION: Synthetic DNA

<400> SEQUENCE: 19
agtgaattcg gatttaaatg tatgcggcat gtcactgggt tttgccgacc cggaagcgat     60
cgagaaccag ctgaccacgg aacgtgagcc ggtcagcggg ttcgcgcgtt tcctctcata    120
gcaaagtttg agaaaagttt gtatcaatgt gtaacgatga gtgccgatat acaagacgac    180
gtccgtgtat tggctgggag tgttccaagg ggcagcaagg tgaacccggg tacgcctggg    240
gcaagccaga ggcggttcgc atgcaaacgt gaccttttgg ttgcttttc cgcaatgtgg    300 aaatgtttgc aaatcgaact taaggagcg tctgtaagtc tttaatcttg ctaacaattt    360 cttttctttcc tacactagcg ccattcctat gcgctgaacg aatcatgttc cggtctgatt    420 ccatttttc cagattcttc ggctccgcac ccctgtccgc tgttgccacc gcggtcctgg    480
tatcgtacgg aacgcctgac cgggaaaaaa cgcgccgtgc cacggcgcgt ttttcgttct    540
ggcggccgcg gccgtcagag cagcttgcct gggttcatga tcccggccgg gtcgaacacg    600
```

| | |
|---|---|
| gccttgatct cgcgcatcag ccgcagttcc agcgggtcct tcatggtcag gaaggcatgg | 660 |
| cgcttgagct ggccgatgcc atgctcggcg ctgatgctgc cgccgtagcg catcacttcg | 720 |
| tccagcaccg cgtcggtcac cgcatcgcct tgcgtggccg cccagtcctt gggcgcgccg | 780 |
| gccgggcgcg acaggttgta gtgcaggttg ccgtcgccga agtgcccgaa gataaagggc | 840 |
| cggatggcgg gatcgagccc acgcagccgc gtttccatcg aggtcatgaa ggccggaatc | 900 |
| tgctcgatcg ggagcgagat gtcgtgcttc aggtgcgatt taaatggata gctcgg | 956 |

```
<210> SEQ ID NO 20
<211> LENGTH: 223
<212> TYPE: DNA
<213> ORGANISM: Artificial Sequence
<220> FEATURE:
<223> OTHER INFORMATION: Synthetic DNA

<400> SEQUENCE: 20
```

| | |
|---|---|
| agtgaattcg gatttaaata gggcctgctt gcccaggtcc ggctgccgct gctctgcgcc | 60 |
| accgccctgc tgctggcggc ctgcgccagt tccccgtctt cgcgccacgc cggcctgccg | 120 |
| cggacgccgg gcaaacccat gatcgacccc agcgccggac tggaagagat ttcgatccag | 180 |
| gcgatgtccc tggtcggcac acccatttaa atggatagct cgg | 223 |

```
<210> SEQ ID NO 21
<211> LENGTH: 238
<212> TYPE: DNA
<213> ORGANISM: Artificial Sequence
<220> FEATURE:
<223> OTHER INFORMATION: Synthetic DNA

<400> SEQUENCE: 21
```

| | |
|---|---|
| agtgaattcg gatttaaata gcgatcggta cttcattccc tggcgcgtgc cgccgtcgga | 60 |
| attgccattg tctgcggtgc gactgtgtcg aatggagtgc tggcggatac ggtattcaag | 120 |
| gatgccgacg cccgtatcga tgccacggcc cacgccgcgg attcgcatgc ggaaggcaag | 180 |
| cgcggcttgc tgtcgtcggt ggtgaattcc accagcaaca tttaaatgga tagctcgg | 238 |

```
<210> SEQ ID NO 22
<211> LENGTH: 926
<212> TYPE: DNA
<213> ORGANISM: Artificial Sequence
<220> FEATURE:
<223> OTHER INFORMATION: Synthetic DNA

<400> SEQUENCE: 22
```

| | |
|---|---|
| agtgaattcg gatttaaata cccctatacg cgcaagctga tggcggcggc gcaggtcggc | 60 |
| gctggctgac ccggaggtgt gcggcgcagc aacgccgcgg ccccgcctgg ctagcatccg | 120 |
| gttgttcgga tcaatccgat aaacaaggtg cgaattcccg cctatatcct tgattcgcca | 180 |
| gtcaaatccg gcgaatttgt aacgaacttt gacatgtgaa tgacaaccct ttaccatccc | 240 |
| gcgagaacta gttttggggg tggtccgtcc gacgcattgg atcgtgcata gcacgtttgc | 300 |
| ggtgcaagac aggcccggaa agcctggtgc ggatgttgca tagggttcac cccgcaggtt | 360 |
| cacatgaatt tctcgcgaag ttcacgcgaa tttcacatat aaccagctgc ccggacttg | 420 |
| tgccggggct tgctttggaa cgatcaacgg agaaccagt ttccggcgcg ctacaagcaa | 480 |
| aaaggactgc tgcgacagtc cttttttctt tggcggggcg tgctcccgg gctattgcac | 540 |
| tgcgaccgtt ccgccggtg ccaggcgggc ctgttccagc cgctgccgca gcgttgccat | 600 |
| caccgccgtg gtggcctgtt cgccggccag tatggctcgg ttgcgggcgt tgaagtcgct | 660 |

```
gccgcccata tcgggcagct cggggcggat caccacgtcg gcgcgcgcca gtgccatctt    720
gttgatcgac tggcccatga tcgcggtggt ctgcagcagc acgccgctct ggcccgcgtt    780
cttctgcgcc gacgggtcgg ccgagatgtt gaccgcgatg acaaagtccg cgcccatgcc    840
gcgcgcggaa tccaccggca ccggctcgac caggccgccg tcgacatagt cgtgaccctg    900
gatcgacatt taaatggata gctcgg                                         926
```

<210> SEQ ID NO 23
<211> LENGTH: 2478
<212> TYPE: DNA
<213> ORGANISM: Artificial Sequence
<220> FEATURE:
<223> OTHER INFORMATION: Synthetic DNA

<400> SEQUENCE: 23

```
agtgaattcg gatttaaatg ctaatggtga gtgtggtctt ggacatcgcg cctcctttac     60
tgcttgttgc cgctaatggc cgcgcaccta tgcagtgcat ccggcaggca ccagtctgaa    120
gccgctgcgc gcaacgcgcc gcgaagcggc gccatgccca tgcgccaggc gcatgcctcg    180
ctacttgcgc ggcattgtcc gcccgctcac agcacaatgc gcaaggcgcg tgccaggcat    240
aaactgatgg ccaattgtac gccgccccct gaccaggaac gccgggccag tcccggcgtt    300 ttttttattct atagcgcaat taaccgccgt catattgcgt caccatgatt gccggatggc    360
cgcggcgatc ccttgctgga ggccggttcc aagaagattt aaagatgtca cggaattgtc    420
atacagggag catagagttc gtcttgtcaa aaatttgtca ttcccaacca atgttctctg    480
gaggacatat gtcccagaag aaatcgccac gcttcgagct gcgcagtggc aacgtagacg    540
ccctccttct cgccctccag accgccgaca tggctgcgct gcgggatgac ctcctcgccc    600
gctttgaagc caccccgac ttcttttcca atgacgtgat tgcgctggac ctgcgcgcgc    660
tggaagatga cagcgaagtc gcgcttggca ccgtgatcga gacgcggcc acgctcaggg    720 cccgcgccat cggcgtggtg gcccgccccg gccagcgcga gtgggccgag cgcttcggcc    780
tgccgctgct ggacagccag gcccgccgcg gcagtggcgc cgatcgcgcc accgaccgtg    840
ccgccgaggc cagggccgca gccgcggcgg aacaggccgc agccgaccag gccgcgcgcg    900
aggaatccat ccgcgccgcc gcgcaggcca ccaccgacgc cgccgtggcc gctgccatcc    960
gccagaccca gaccatgctg atcgacaagc cgcttcgctc gggccagcag gtctacgcgc   1020
agggcgacgt ggtcatcctg gacgtggtca gctacggcgc cgaggtgatc gccgaaggca   1080
acatccatat ctatgccccg ctgcgcggcc gtgcgctggc gggcgtcaag ggcaacaccg   1140
gcgcgcgcat tttcagcacg tgcatggagc ctgaactgat ttccatcgcc ggcatctacc   1200
ggaccgcgga gcagacgctt ccggccgacg tgctcggcaa gaccgcccag gtgcgcctgg   1260
ccgatgaaaa actgatcctg gaagcgctgc ggctcaagta accgcggcag cccccgggac   1320
cgaattgcag agagcgcaag cttcaactta ttactggacc aaagagccat ggcaaaaatc   1380
atcgttgtga cctccggcaa gggaggcgtc ggcaagacca ccaccagcgc cagctttgcc   1440
gccggcctgg ccctgcgcgg ccacaagact gccgtgatcg acttcgacgt cggcctgcgc   1500
aaccttgacc tgatcatggg ttgcgagcgc gcgtggtgt acgacctgat caacgtggtg   1560
cagggcgaag ccaacctgcg ccaggcgctg atcaaggaca agaagtgcga gaacctgttc   1620
atcctgccgg cctcgcagac gcgcgacaag gacgcgctca cgcgcgaagg cgtcgagaag   1680
gtcatcaacg gcctgatcga gatggatttc gaattcatca tctgcgactc gccggccggc   1740
```

-continued

```
atcgagtcgg gcgcgctgat ggcgatgtac ttcgccgacg aggcgctgat cgtgaccaac      1800
ccggaagtgt cgtcggtgcg cgattcggac cgcatcctgg gcatcctggc ctccaagacc      1860
aagcgcgcca gcgaaggcgg cgacccgatc aaggaacacc tgctgatcac ccgctacaac      1920
cccaagcgtg tgcatggcgg cgaaatgctg tcgctgaccg acatccagga aatcctgcgc      1980
atcaagctga tcggcgtggt gccggagtct gaagccgtgc tgcacgcctc gaaccagggc      2040
acgcccgcca tccacctgga aggcagcgac gtggccgacg cctatggcga cgtggtggac      2100
cgcttcctcg gcaaggacaa gccgatgcgt ttcaccgact accagaagcc gggtctgctc      2160
tcccgcatct tcggcaacaa gtaacctgcc ggcctggttc aaccagtcgg cagccgacta      2220
gtcccggcag ccgccagcgc gctggcctcg cttatcatgg cagctgcgcc gggcggcacg      2280
cgaacggcgc ggcaccaacg atcaacatgc cattgctacc gacacaagac ttccagggcc      2340
agccgctggt ccggatcggc gatgccgaca cgttcctgct gctcgcccccg caacacggcg      2400 ggcggctggt ccgctgggtg caccgcggac aggacatcct ctactggccg gacgctgcca      2460
tttaaatgga tagctcgg                                                    2478
```